(12) United States Patent
Ilyin et al.

(10) Patent No.: US 9,686,978 B2
(45) Date of Patent: Jun. 27, 2017

(54) PLATELET CONCENTRATE PRESERVATION METHOD

(71) Applicant: Advanced Preservations Technologies, LLC, Buffalo, NY (US)

(72) Inventors: Ilya Ilyin, Wayland, MA (US); Igor Kachko, St. Petersburg (RU); Alexander Shumeev, St. Petersburg (RU); Yuri Punin, St. Petersburg (RU); Stanislav Kolchanov, St. Petersburg (RU)

(73) Assignee: Rich Technologies Holding Company, LLC, Buffalo, NY (US)

( * ) Notice: Subject to any disclaimer, the term of this patent is extended or adjusted under 35 U.S.C. 154(b) by 0 days.

(21) Appl. No.: 14/648,804

(22) PCT Filed: Dec. 11, 2013

(86) PCT No.: PCT/US2013/074251
§ 371 (c)(1),
(2) Date: Jun. 1, 2015

(87) PCT Pub. No.: WO2014/099515
PCT Pub. Date: Jun. 26, 2014

(65) Prior Publication Data
US 2015/0305324 A1  Oct. 29, 2015

Related U.S. Application Data

(60) Provisional application No. 61/739,327, filed on Dec. 19, 2012.

(51) Int. Cl.
| | |
|---|---|
| *A01N 1/02* | (2006.01) |
| *A61J 1/16* | (2006.01) |
| *A61J 1/14* | (2006.01) |
| *A61J 1/10* | (2006.01) |
| *A61M 1/02* | (2006.01) |

(52) U.S. Cl.
CPC ........... *A01N 1/0289* (2013.01); *A01N 1/021* (2013.01); *A01N 1/0263* (2013.01); *A61J 1/10* (2013.01); *A61J 1/1468* (2015.05); *A61J 1/16* (2013.01); *A61J 1/165* (2013.01); *A61M 1/0272* (2013.01); *A61M 1/0277* (2014.02); *A61M 2202/0208* (2013.01); *A61M 2202/0291* (2013.01); *A61M 2202/0427* (2013.01)

(58) Field of Classification Search
None
See application file for complete search history.

(56) References Cited

U.S. PATENT DOCUMENTS

| | | |
|---|---|---|
| 2008/0171726 A1 | 7/2008 | Roth et al. |
| 2010/0009334 A1 | 1/2010 | Ilyin et al. |
| 2010/0196996 A1 | 8/2010 | Kilic et al. |

FOREIGN PATENT DOCUMENTS

| | | |
|---|---|---|
| WO | 2013049118 | 4/2013 |

OTHER PUBLICATIONS

Hess, John R., "Conventional blood banking and blood component storage regulation: opportunities for improvement" Bood Transfusion; 8:Suppl, 3:s9-s15 (2010).
European Searching Authority, Supplementary European Search Report for corresponding application EP No. 13865922.2 (Jul. 28, 2016).
U.S. Searching Authority, International Search Report and Written Opinion for corresponding PCT Application No. PCT/US2013/074251 (May 21, 2014).

*Primary Examiner* — Renee Claytor
*Assistant Examiner* — Sharon M Papciak
(74) *Attorney, Agent, or Firm* — Fay Sharpe LLP

(57) ABSTRACT

A method and a platelet concentrate preservation device for platelet concentrate storage. A method includes at least partially saturating platelet concentrate xenon, and storing the platelet concentrate at less than 15 C in a generally horizontal position. A device can be used to store blood, blood products, or combinations thereof that may or may not be under pressure. The device includes a chamber having a cavity. The chamber includes first and second chamber parts that form the cavity when releasably connected together. The cavity is designed to receive at least one bag that contains the blood, blood products, or combinations thereof. The device also includes a high-strength casing and includes a chamber cavity. The high-strength casing includes first and second casing parts that form the chamber cavity when releasably connected together. The chamber cavity is designed to receive the chamber.

51 Claims, 6 Drawing Sheets

PLATELET CONCENTRATE PRESERVATION METHOD

The present invention claims priority on U.S. Patent Application Ser. No. 61/739,327 filed Dec. 19, 2012, which is incorporated herein by reference.

The present invention refers to the field of medicine (in particular, to apheresis) and could be used for platelets preservation in the form of platelet concentrate.

BACKGROUND OF THE INVENTION

A method for preserving cells and cell cultures (described in PCT Patent Application Publication No. WO/2012/109107, which is incorporated herein by reference) is known. The method was developed for reducing apoptosis in nucleated cells. The method entails holding nucleated cells in a container and adding a gas containing xenon to the container so that the pressure inside the container reaches between 0.5 to 4.0 atm. above ambient pressure; holding the container at between 0.5 to 4.0 atm. above ambient pressure for a period of time during which the temperature in the container is between 22° C. and 37° C.; lowering the temperature in the container to between 0.1° C. and 10° C. while maintaining the pressure of 0.5 to 4.0 atm. above ambient pressure and holding the container for a period of time; and reducing the pressure in the container to ambient pressure and increasing the temperature to 22° C. to 37° C. By performing these steps, the patent application discloses that the cells undergo less apoptosis than compared to cells that do not undergo such a treatment. The implementation of this method involves placing the cells in a container capable of withstanding up to 4.0 atm. of excess pressure in relation to atmospheric pressure. It is known that the standard platelet storage method involves storing platelets in a bag. The seams of such standard bags do not allow using this bag for implementing the above-indicated storage method. The creation of a bag capable of withstanding the above-mentioned high pressure would increase the bag cost, which is highly undesirable because these bags are single-use products. Also, this method is mainly intended for preserving nucleated cells, while the platelets are anucleated cells.

A method for preserving platelets described in US Patent Publication No. 2010/0009334, (which is incorporated herein by reference) is known. This method involves the preparation of platelet plasma out of the whole donated blood; keeping the platelet plasma in a gas medium containing from 65% to 100% of xenon under pressure for approximately 3.5 to 5 bars; subsequently cooling the platelet plasma down to a temperature of approximately 3° C. to 6° C.; and storing the platelet plasma range under the conditions of the above-indicated temperature and pressure of gas medium. US 2010/0009334 discloses that the method is implemented by placing the platelet concentrate in a gas-impermeable container into which a xenon-containing gas medium is fed under pressure. US 2010/0009334 also discloses the use of conventional gas-permeable bags intended for storing biological fluids (in particular, blood and blood components) and placing the gas-permeable bags in a gas-impermeable container into which a xenon-containing gas medium is fed under pressure. This method provides storage of platelets during a period of at least one week, which may not be long enough for some applications. Secondly, this method is best performed on small volumes of platelet concentrate—of the order of units of ml (i.e., placed into a vial, for example). It is believed that a sufficient amount of oxygen (required for maintaining metabolic processes in plasma) stays in a vial partially filled with such volume of platelet plasma. However, in actual practice, the platelets are required to be stored in standard bags with a volume of at least 200 ml, not in small vials. When the platelets are stored in bags, the amount of oxygen available for platelets may be insufficient for aerobic respiration, which can limit the duration of platelet plasma storage.

Another method for preserving platelets in the gas mixture (PCT Application No. PCT/US2012/057211 [WO 2013/049118] which is incorporated herein by reference) is known. According to this method, a platelet concentrate (obtained in advance from whole human blood) is kept in a gas mixture with xenon content from 79% to 95% and oxygen content from 5% to 21% under pressure from 3.5 to 5 bars at a temperature from 18° C. to 23° C., after which it is cooled down to a temperature from 3° C. to 6° C. and placed for storage under the conditions of the above-indicated composition and pressure of gas mixture and at above-indicated temperature. In this method, oxygen serves as a component of the gas mixture, in which the gas-permeable bag with platelet concentrate is stored. A design of the storage device for this method is not described.

A method and device for preserving blood or its components in a gas medium under pressure and system for the same (PCT Application No. PCT/US2012/043449 [WO 2012/177820] which is incorporated herein by reference) is known. According to this invention, blood or blood components are placed in a bag that is made of a xenon gas-permeable material. The bag is then placed into a hermetically-sealed cylindrical chamber into which xenon-containing gas (with a xenon content of at least 65%) is fed under pressure until the pressure in the chamber reaches the value approximately from 3.5 bars to 5 bars, after which the chamber is placed for storage at a temperature within the range from 3° C. to 6° C. Bags that are made of the gas-permeable material that are designed to allow xenon to pass through the bag are used for the implementation of this method. In this method, the xenon-containing gas (fed under pressure into the chamber) passes through the bag wall, after which blood or blood components in the bag are saturated with xenon. According to this method, the bag with the blood or blood components is placed in a cylindrical chamber and, during storage, the chamber is positioned vertically. The bag in the chamber is also positioned vertically, and the blood or blood components are not stirred in the course of storage. The absence of stirring and the vertical position of the bag in the course of storage can lead to a situation in which the platelets get deposited on a small area of the bag bottom, thus forming a dense deposit by the end of the storage period. Platelets in such a deposit can change their properties and a considerable part of the platelets can be activated and stick together. Platelets that are stuck to one another produce micro-aggregates which can result in the reduction in the number of free platelets, which in its turn, can lead to a decrease in platelet concentrate efficiency. Moreover, the sticking together of the platelets can lead to the formation of aggregates of quite considerable size, which could be detrimental for a recipient because, after transfusion, such aggregates may be capable of clotting the blood vessels, thus leading to disturbed blood circulation.

In view of the current state of the art, there is a need for a method for preserving platelet concentrate under pressure that does not lead to the formation of a dense deposit and aggregates of platelets.

SUMMARY OF THE INVENTION

The present invention is directed to the development of a method for preserving platelet concentrate involving the use of a gas mixture (e.g., xenon and oxygen) under pressure that does not lead to the formation of a dense deposit and aggregates of platelets.

In one non-limiting aspect of the present invention, there is provided a platelet concentrate preservation method which includes stages of platelet concentrate packaging, treatment of packaged platelet concentrate with a gas mixture containing xenon and oxygen, and storage of treated platelet concentrate and preparation for use. In accordance with the non-limiting process of the present invention, the platelet concentrate is placed in a hermetically-sealed bag (made of material that is permeable to xenon and oxygen). The bag can optionally have a general shape of a flat container. The bag with the platelet concentrate can then be optionally placed in a hermetically-sealed chamber, into which a gas mixture of xenon and oxygen. The content of the xenon in the gas mixture is greater than the xenon content in the air at sea level. In one non-limiting aspect of the invention, the xenon content of the gas mixture is at least 5% by volume and up to 99.99% by volume (e.g., 5%, 5.001%, 5.002% . . . 99.988%, 99.989%, 99.99%) and any value or range therebetween. In another non-limiting aspect of the invention, the xenon content of the gas mixture is from about 50% to 99.9% by volume, typically about 55% to 99% by volume, more typically about 60% to 98% by volume, yet more typically about 70% to 97% by volume, and still yet more typically about 79% to 95% by volume. In still another non-limiting aspect of the invention, the oxygen content of the gas mixture is at least about 0.01% by volume. In yet another non-limiting aspect of the invention, the oxygen content of the gas mixture is about 0.01% to 50% by volume (e.g., 0.01%, 0.011%, 0.0112% . . . 49.998%, 49.999%, 50%) and any value or range therebetween. In still yet another non-limiting aspect of the invention, the oxygen content of the gas mixture is about 0.1% to 45% by volume, more typically about 2% to 40% by volume, still more typically about 3% to 30% by volume, and yet still more typically about 5% to 21% by volume. The gas mixture generally includes 0% to 5% by volume (e.g., 0%, 0.0001%, 0.0002% . . . 4.998%, 4.999%, 5%) and any value or range therebetween of a gas that is other than xenon or oxygen. In another non-limiting aspect of the invention, the gas mixture is fed under pressure at a pressure that is greater than atmospheric pressure at sea level (e.g., 1 atm.). In still another non-limiting aspect of the invention, the gas mixture is fed under pressure at a pressure that is 1 to 20 bars (e.g., 1 bar, 1.01 bars, 1.02 bars . . . 19.98 bars, 19.99 bars, 20 bars) and any value or range therebetween greater than atmospheric pressure at sea level. In yet another non-limiting aspect of the invention, the gas mixture is fed under pressure at a pressure that is about 1.01 to 20 bars greater than atmospheric pressure at sea level, more typically about 1.1 to 15 bars greater than atmospheric pressure at sea level, still more typically about 1.5 to 10 bars greater than atmospheric pressure at sea level, yet still more typically about 2 to 8 bars greater than atmospheric pressure at sea level, and further more typically about 3.5 to 5 bars greater than atmospheric pressure at sea level. In another non-limiting aspect of the invention, the gas mixture is fed to the bag at a temperature of generally at least about 15° C. In still another non-limiting aspect of the invention, the gas mixture is fed to the bag at a temperature of 15° C. to 35° C. (e.g., 15° C., 15.01° C., 15.02° C. . . . 34.98° C., 34.99° C., 35° C.) and any value or range therebetween. In yet another non-limiting aspect of the invention, the gas mixture is fed to the bag at a temperature of about 18° C. to 35° C., and more typically about 20° to 24° C. In another non-limiting aspect of the invention, the platelet concentrate is generally kept under the conditions of the above-indicated gas mixture composition, gas mixture pressure and temperature until the platelets are partially saturated (e.g., 50%, 60%, 70%, 75%, 80%, 85%, 90%, 95%, 98%, 99%, etc.) or fully saturated with xenon. Thereafter, the bag with platelet concentrate is cooled down to a temperature below about 15° C. and above the freezing point of the platelet concentrate in the bag (e.g., about 0° C.) and any value or range therebetween (e.g., 0.01° C., 0.02° C., 0.03° C. . . . 14.97° C., 14.98° C., 14.99° C.) and then placed for storage. In still another aspect of the invention, the bag with platelet concentrate is cooled down to a temperature of 0.01° C. to 15° C., more typically about 1° C. to 10° C., and still more typically about 3° C. to 6° C. and then placed for storage. In yet another non-limiting aspect of the present, the bag of platelet concentrate while in storage is optionally placed in a generally horizontal position (with flat side down) under the conditions of the above-indicated composition and above-indicated gas mixture, gas pressure and temperature. For purposes of the present invention, the horizontal position is defined as the longitudinal axis of the bag is positioned horizontal to a ground surface (e.g., earth surface). Prior to using the preserved platelet concentrate after the storage of the platelet concentrate, the contents of the bag can optionally be stirred (e.g., placing the bag on a shaker, shaking the bag with platelet concentrate, etc.). Prior to using the preserved platelet concentrate after the storage of the platelet concentrate, the excess gas pressure in the bag is generally released. Prior to using the preserved platelet concentrate after the storage of the platelet concentrate, the bag with platelet concentrate can for a time period (e.g., 0.001-20 hours) and any value or range therebetween, to warm up (e.g., naturally warmed up, etc.) to a temperature (e.g., 12° C. to 35° C.) and any value or range therebetween at which it is permissible to use the platelet concentrate.

One non-limiting distinctive feature of the method of the present invention includes the fact that with this method, the bag with platelet concentrate (e.g., having a general shape of a flat container) can be stored in horizontal position (i.e., with flat side facing down), and prior to using the platelet concentrate, it can be first stirred and then the pressure excess of the gas mixture can be released. With such an approach to storage, a minimal thickness of any deposit formed in the process of platelet sedimentation during storage is ensured. Any diffused deposit that forms in the bag can be easily disintegrated in the course of stirring or shaking the contents of the bag, and the use of pressure excess of the gas mixture in the bag makes it possible to avoid intensive bubble generation during stirring and/or shaking of the bag.

In another and/or alternative non-limiting aspect of the present invention, there is provided a device for preserving blood products that is designed to be able to preserve blood products in a gas medium under pressure. The device for preserving blood products includes a chamber that can be hermetically-sealed and high-strength casing that is designed to partially or fully receive the chamber. In one non-limiting embodiment of the invention, the chamber can be formed of one or more parts. In one non-limiting aspect of this embodiment of the invention, the chamber is formed of two parts that are designed to be joined together in such a way that after the joining of the two parts, the two parts form a cavity. The cavity can be an airtight cavity. The cavity is designed to partially or fully accommodate a bag that contains a blood product. The bag that contains the blood product can be formed of a gas-permeable material; however, this is not required. The chamber (e.g., hermetically-sealed chamber) can optionally include an inlet channel that fluidly connects the cavity to the exterior of the chamber. The inlet channel can be used to feed gas into and/or remove gas from the cavity. In another non-limiting embodiment of the invention, the high-strength casing can include one or more parts. In one non-limiting aspect of this embodiment of the invention, the high-strength casing includes two parts that are intended to be joined together. One or both parts of the high-strength casing can include a pocket. The pocket is generally located in the central area of one or both parts; however, this is not required. The pocket is designed to partially or fully receive the chamber. In one non-limiting design, the one or more pockets are designed to fully receive the chamber such that when the one or more parts of the high-strength casing are connected together, the chamber is fully encompassed in the one or more pockets of the one or more parts of the high-strength casing. The connection of the pockets forms the chamber cavity for the chamber. The design of the pockets is non-limiting. In one non-limiting design, the total depth of the one or more pockets is sufficient to fully place the chamber into the one or more pockets, and the height of the one or more pockets is such that a minimal gap is formed between the inner surface of the one or more pockets and the outer surface of the chamber when the chamber is inserted into the one or more pockets; however, this is not required.

Due to the fact that the device for preserving blood products includes at least two components—namely, a chamber and a high-strength casing (which two components perform different functions), the device for preserving blood products in accordance with the present invention has resulted in the formation of an all-purpose, reliable, easy-to-manufacture and easy-to-use device that can be used in the preservation of blood and/or blood components. The chamber is designed to contact a bag that includes a blood product. One non-limiting desirable design requirement of the chamber is a low-cost design. This non-limiting requirement can be satisfied since the chamber is not required to be designed to withstand large forces. As such, the chamber can be formed or include inexpensive materials (e.g., plastics, coated paper or paper board, etc.) that are formed into the chamber by using highly productive technologies (e.g., casting, die molding, stamping, compression molding, etc.); however, this is not required. The main load arising in the course of filling the chamber with gas is exerted upon the high-strength casing, into which the chamber is placed.

The casing can be made of various high-strength materials (metal, wood, composite materials, ceramic, fiber reinforced materials, etc.). These materials can be formed by various processes (molding, stamping, welding, extrusion, etc.). Generally, the high-strength materials used to form the casing are at least about 2 times stronger and at least 2 times more rigid (e.g., 2-10,000 times, 5-1000 times, 10-500 times, 20-100 times, etc.) than the materials used to form the chamber when similar thickness materials are compared; however, this is not required. Generally, the high-strength material used to form the casing is made of a different material from the material used to form the chamber; however, this is not required. Generally, the high-strength material is a thicker material and/or a more rigid material than the material used to form the chamber; however, this is not required.

The pockets of the one or more parts of the high-strength casing (into which the chamber is placed) are made deep enough for the accommodation of the chamber, while the height of the one or more pockets is sufficient to place the chamber into the pockets while maintaining a minimal gap between the interior surface of the one or more pockets and the outer surface of the chamber. Such gap is generally at least about 0.001 inches and typically no more than about 0.5 inches and any value or range therebetween (e.g., 0.001 inches, 0.0011 inches, 0.0012 inches . . . 0.4998 inches, 0.4999 inches, 0.5 inches). In one non-limiting arrangement, the gap is about 0.001-0.25 inches, and typically about 0.01-0.1 inches.

The design of the high-strength casing generally results in the transfer of the load (arising in the course of filling the chamber with gas and the gas acting on the chamber walls) directly to the high-strength casing. The design of the high-strength casing generally results in the prevention of significant deformation and damage to the chamber during the introduction, maintaining and removal of gas; however, this is not required. The high-strength casing can be designed to be a reusable unit; however, this is not required. The chamber can also be designed to be a reusable unit; however, this is not required. When the high-strength casing is designed to be a reusable unit, it is more acceptable that the cost be higher than that of the chamber, which is generally a disposable component; however, this is not required. As such, the high-strength casing is generally formed of more expensive materials to ensure the required strength and durability of the high-strength casing.

In still another and/or alternative non-limiting aspect of the invention, the size and shape of the cavity (e.g., airtight cavity) that is formed after the parts of the chamber are joined together closely or exactly to match the size and shape of the bag with blood product that is to be placed in the cavity; however, this is not required. For example, when taking the shape of standard bags for blood products into account (which is close to a generally rectangular shape in a plan view), the chamber can be shaped generally as a parallelepiped, the legs of which are characterized by proportions close to those characterizing sides of the bag filled with blood product, and both parts of the chamber can be made essentially flat. The cavity can also include recesses in the central area of the cavity. The recesses form the cavity (e.g., air-tight cavity, etc.) that is designed to accommodate a bag containing blood product when positioned in the cavity of the chamber. In one non-limiting embodiment, the size and shape of the cavity is designed such that, when the bag is placed in the cavity, at least about 75% of the volume of the cavity is filled by the bag; however, this is not required. In one non-limiting aspect of the invention, about 75%-100% (e.g., 75%, 75.01%, 75.02% . . . 99.98%, 99.99%, 100%) and any value of range therebetween, of the volume of the cavity is filled by the bag.

In yet another and/or alternative non-limiting aspect of the invention, the chamber can be designed to form a hermetically-sealed cavity when one or more parts of the chamber are connected together; however, this is not required. In one non-limiting design, the air tightness of the cavity is formed by a sealing arrangement (e.g., sealing ring, groove arrangement, etc.) between the one or more parts of the chamber. One non-limiting sealing arrangement is the result of joining the parts of the chamber together, which parts include annular grooves that are made along the perimeter of each part of the chamber. After both parts of the chamber are joined together, the grooves form an annular channel into which a gasket is laid (the latter is shaped as a ring or the like made of flexible material—e.g., rubber, polymer material, etc.). As can be appreciated, other or additional arrangements can be used for the air-tight cavity.

In still yet another and/or alternative non-limiting aspect of the invention, the parts of the high-strength casing can be embodied as a honeycomb structure produced by strengthening ribs oriented in one or more planes (e.g., three orthogonal planes, etc.) and forming the pocket in the high-strength casing that is designed to receive the chamber; however, this is not required. In such a configuration, the high-strength casing allows for the reduction of weight and the material needed for the manufacturing of the high-strength casing and still achieves the desired strength and durability of the high-strength casing.

In another and/or alternative non-limiting of the invention, the high-strength casing can include connecting flanges to ensure reliable joining of the parts of the high-strength casing; however, this is not required. As can be appreciated, other or additional arrangements can be used to ensure reliable joining of the parts of the high-strength casing. The connecting flanges, when used, can be formed about the pocket of the parts; however, this is not required. Many different arrangements can be used to connect the flanges together, when used. For example, the flanges could include fastening elements. One non-limiting design for a fastening element is that one flange could be equipped with twist locks made as a fixing catch (secured in such a way that it can be turned) on a bar installed perpendicular to the plane of flanges joined, while matching cuts are made in the other flange for the twist locks. For such an arrangement, when joining the flanges together, the twist locks located on one flange are passed through matching cuts made in the other flange when the parts of the high-strength casing are positioned together. After connecting the flanges together, the catches are turned and the catches become engaged with the rear side of the flanges, thereby releasably securing together the parts of the high-strength casing. As can be appreciated, many other arrangements can be used to releasably secure together the parts of the high-strength casing. In one non-limiting arrangement, when the parts of the high-strength casing are connected together, a chamber cavity is formed that is designed to receive the chamber that holds the bag of blood and/or blood products. In one non-limiting arrangement, the chamber cavity is hermetically-sealed when the parts of the high-strength casing are connected together; however, this is not required. In one non-limiting design, the air tightness of the chamber cavity is formed by a sealing arrangement (e.g., sealing ring, groove arrangement, etc.) between the one or more parts of the high-strength casing. The size and shape of the chamber cavity that is formed after the parts of the high-strength casing are connected together closely or exactly match the size and shape of the chamber that is to be placed in the chamber cavity; however, this is not required. In one non-limiting embodiment, the size and shape of the chamber cavity is designed such that when the chamber is placed in the chamber cavity and the parts of the high-strength casing are connected together, at least about 50% of the volume of the chamber cavity is filled by the chamber; however, this is not required. In one non-limiting aspect of the invention, about 75%-100% (e.g., 75%, 75.01%, 75.02% . . . 99.98%, 99.99%, 100%) and any value of range therebetween, of the volume of the chamber cavity is filled by the chamber.

In still another and/or alternative non-limiting aspect of the invention, the high-strength casing can include one or more fittings that provide fluid communication with the chamber when the parts of the high-strength casing are connected together; however, this is not required. In one non-limiting configuration, the one or more fittings, when used, could be installed on the end face of one part of the high-strength casing. The one or more fittings can include a channel that fluidly connects the chamber in the high-strength casing to the outside of the high-strength casing. The fitting can also be designed so as to be positioned in such a way that when the chamber is positioned in the chamber cavity (that is formed by the pockets of the parts of the high-strength casing), the fitting is fluidly connected to the inlet channel that fluidly connects the chamber cavity to the exterior of the high-strength casing. This connection between the fitting and the inlet channel can be an air-tight connection; however, this is not required. Such an arrangement enables gas to be inserted into and/or removed from the interior of the cavity of the chamber via the fitting and the inlet channel. The fitting can optionally have a projecting part on its inner side which matches the recess made in the chamber and connected with the inlet channel, and the connection can optionally be provided via the use of a sealing gasket laid into the annular groove made on the side surface of the projecting part. As can be appreciated, many other arrangements can be used. Also, a one-way valve can optionally be installed on/included in the fitting which can be used to allow the pumping of gas into the cavity of the chamber and, on the other hand, prevent gas egress from the cavity.

In yet another and/or alternative non-limiting aspect of the invention, the high-strength casing can include an end-to-end inlet channel that is located on one or more parts of the high-strength casing; however, this is not required. This channel can be designed to be oriented generally perpendicular to the horizontal plane of a side of the high-strength casing; however, this is not required. A side channel can be provided that abuts to the end-to-end channel, and the side channel can be designed to be oriented in the direction of the pocket of the part of the high-strength casing and terminate at a location where the inlet channel in the high-strength casing is connected. The end fittings can optionally include valves (e.g., one-way valve, etc.) through which gas can be fed into the high-strength casing and chamber. The one or more valves can be installed on one or both ends of the end-to-end inlet channel. Another fitting can optionally be installed in the side channel. This fitting can be designed for an airtight connection with the inlet channel of the chamber; however, this is not required. Such a non-limiting configuration can be used such that, after the chamber is placed into the chamber cavity of the high-strength casing, the cavity (e.g., airtight cavity) of the chamber is fluidly connected with the end-to-end inlet channel into which gas can be fed through and/or released from one of the end fittings. In one non-limiting design, the end fittings can be quick-disconnect couplings. As can be appreciated, the end fittings can have other configurations. In this particular design, an end fitting on the device for preserving blood products can be made in such a way that an airtight connection with an end fitting of another device is formed. This arrangement provides an opportunity to assemble several devices for preserving blood products in a stack by fastening them to one another by means of their end fittings. Thus, the end-to-end inlet channels of the devices for preserving blood products can be connected in series, thus forming a single inlet channel, through which gas can be fed concurrently into all these devices. As can be appreciated, other connection arrangements for a plurality of devices for preserving blood products can be used.

In still yet another and/or alternative non-limiting of the present invention, the high-strength casing can include a drainage or release valve in which the end-to-end inlet channel is arranged; however, this is not required. The drainage or release valve can be used to release gas from the chamber; however, this is not required. In this non-limiting design, the drainage or release channel can be oriented to abut to the end-to-end inlet channel and to connect to the outer surface of a part of the high-strength casing, thus connecting the end-to-end inlet channel with the ambient atmosphere. The drainage or release valve allows for the releasing of gas from the chamber that is located in the chamber cavity of the high-strength casing when necessary. The drainage valve can be made as a rotary-type valve, the handle of which is located on the external side of a part of the high-strength casing; however, other arrangements can be used.

In another and/or alternative non-limiting aspect of the present invention, the parts of the high-strength casing can include projections on the external side or outer surface of the parts; however, this is not required. The projections, when used, can be oriented in opposite directions relative to the horizontal plane of the high-strength casing; however, this is not required. The projections can be used to assemble together several devices for preserving blood products in a stack configuration. In this non-limiting design, projections on one device for preserving blood products are shifted in the horizontal plane relative to the projections on another device for preserving blood products in such a way that when arranging several devices in a stack, the projections of one device interact with the projections of the other device (located above the first one). As such, two or more devices can be stacked on top of one another by use of the projections on the devices. In such an arrangement, the projections facilitate in keeping the stacked devices in place relative to one another. Additionally, the projections can be equipped with fasteners (e.g., screws, clamps, clips, etc.) to ensure a higher reliability of connecting together the stacked-together devices (needed, for example, for transportation purposes); however, this is not required.

The invention is directed to a method for platelet concentrate storage comprising the steps of a) placing a platelet concentrate in a hermetically-sealed bag, wherein the bag is formed of a material that is permeable to xenon and oxygen; b) placing the bag in a sealed chamber; c) feeding a gas mixture into the sealed chamber to at least partially saturate said platelet concentrate with xenon, said gas mixture including xenon and oxygen, said gas mixture having a xenon content that is greater than a xenon content naturally occurring in the atmosphere at sea level, said gas mixture having an oxygen content of at least 0.01% by volume, said gas mixture fed to said sealed chamber under pressure that is greater than atmospheric pressure at sea level, said gas mixture fed to said seal chamber while said platelet concentrate is at least about 15° C.; d) maintaining said bag of platelet concentrate in said sealed chamber in said presence of said gas mixture for at least 0.001 hours; e) after said platelet concentrate has reached a desired saturation of xenon gas, cooling said bag that contains said platelet concentrate to a storage temperature, said storage temperature is less than about 15° C. and greater than a freezing point of said platelet concentrate; f) orienting said bag in a generally horizontal position for a desired time period at said storage temperature; g) warming said bag to ambient temperature; and, h) releasing said pressure in said sealed chamber to allow gas in said bag to reach at least partial equilibrium with said ambient atmosphere. The method can further include the step of shaking, stirring, or combination thereof of said platelet concentrate in said bag prior to a transfusion to a patient. The gas mixture can include about 50% to 99.9% by volume xenon and about 0.01% to 50% by volume oxygen. The gas mixture can include about 55% to 99% by volume xenon and about 0.1% to 45% by volume oxygen. The gas mixture can include about 60% to 98% by volume xenon and about 2% to 40% by volume oxygen. The gas mixture can include about 70% to 97% by volume xenon and about 3% to 30% by volume oxygen. The gas mixture can include about 79% to 95% by volume xenon and about 5% to 21% by volume oxygen. The gas mixture can be fed to said sealed chamber under pressure that is at least 1 bar above atmospheric pressure at sea level. The gas mixture can be fed to said sealed chamber under pressure that is about 1.01 to 20 bars above atmospheric pressure at sea level. The gas mixture can be fed to said sealed chamber under pressure that is about 1.1 to 15 bars above atmospheric pressure at sea level. The gas mixture can be fed to said sealed chamber under pressure that is about 1.5 to 10 bars above atmospheric pressure at sea level. The gas mixture can be fed to said sealed chamber under pressure that is about 2 to 8 bars above atmospheric pressure at sea level. The gas mixture can be fed to said sealed chamber under pressure that is about 3.5 to 5 bars above atmospheric pressure at sea level. The gas mixture can be fed to said sealed chamber while said platelet concentrate is at a temperature of about 18° C. to 35° C. The gas mixture can be fed to said sealed chamber while said platelet concentrate is at a temperature of about 20° C. to 24° C. The gas mixture can be fed to said sealed chamber until said platelet concentrate is at least 50% saturated with xenon gas. The gas mixture can be fed to said sealed chamber until said platelet concentrate is at least 75% saturated with xenon gas. The gas mixture can be fed to said sealed chamber until said platelet concentrate is at least 90% saturated with xenon gas. The gas mixture can be fed to said sealed chamber until said platelet concentrate is at least 95% saturated with xenon gas. The gas mixture can be fed to said sealed chamber until said platelet concentrate is at least 99% saturated with xenon gas. The step of maintaining said bag of platelet concentrate in said sealed chamber in said presence of said gas mixture can be for 0.001-10 hours. The step of cooling down said bag can cool said platelet concentrate to a temperature of 0.01° C. to 15° C. The step of cooling down said bag can cool said platelet concentrate to a temperature of 1° C. to 10° C. The step of cooling down said bag can cool said platelet concentrate to a temperature of 3° C. to 6° C.

The invention is also directed to a method for platelet concentrate storage comprising the steps of a) placing a blood, blood components, or combinations thereof in a hermetically-sealed bag, wherein the bag is formed of a material that is permeable to a gas system; b) placing the bag in a cavity of a chamber, said chamber including first and second chamber parts that form said cavity when releasably connected together; c) placing said chamber that includes said bag into a chamber cavity of a high-strength casing, said high-strength casing including first and second casing parts that form said chamber cavity when releasably connected together; d) feeding said gas system into said cavity of said chamber to at least partially saturate said blood, blood components, or combinations thereof with at least one gas in said gas system, said gas system fed to said sealed chamber under pressure that is greater than atmospheric pressure at sea level; and, e) maintaining said bag of said blood, blood components, or combinations in said cavity of said chamber in said presence of said gas system for at least 0.001 hours. The method can further include the step of f) after said blood, blood components, or combinations thereof has reached a desired saturation of said at least one gas in said gas system, cooling said bag that contains said blood, blood components, or combinations thereof in a cooling system to a storage temperature, said storage temperature is less than about 15° C. and greater than a freezing point of said blood, blood components, or combinations thereof. The method can further include the steps of g) releasing said pressure in said chamber; h) removing said chamber from said chamber cavity; i) removing said bag from cavity of said chamber; and, j) warming said bag above said storage temperature. The method can further include the step of shaking, stirring, or combination thereof of said blood, blood components, or combinations thereof in said bag prior to a transfusion to a patient. The method can further include the step of orienting said bag in a generally horizontal position for a desired time period at said storage temperature. The cavity of said chamber can be a hermetically-sealable cavity. The chamber cavity can be a hermetically-sealable cavity. The method can further include the step of shaking, stirring, or combination thereof of said blood, blood components, or combinations in said bag prior to a transfusion to a patient. The gas system can have a xenon content that is greater than a xenon content naturally occurring in the atmosphere at sea level. The at least one gas that at least partially saturates said blood, blood components, or combinations can be xenon. The gas mixture can include about 50% to 99.9% by volume xenon and about 0% to 50% by volume oxygen. The gas mixture can be fed to said chamber under pressure that is at least 1 bar above atmospheric pressure at sea level. The gas mixture can be fed to said chamber while said blood, blood components, or combinations thereof are at a temperature of about 18° C. to 35° C. The gas mixture can be fed to said chamber until said blood, blood components, or combinations are at least 50% saturated with xenon gas. The step of maintaining said bag of blood, blood components, or combinations in said chamber in said presence of said gas mixture can be for 0.001-10 hours. The step of cooling down said bag cools said blood, blood components, or combinations can be to a temperature of 0.01° C. to 15° C. The chamber can include an inlet channel that fluidly connects said cavity to a casing channel in said high-strength casing to enable a gas source that includes said gas system to be connected to said high-strength casing such that said gas system can flow through said high-strength casing and into said cavity of said chamber. The inlet channel can be hermetically-sealed to said casing channel when said chamber is positioned in said chamber cavity and said first and second parts of said high-strength casing are connected together. The material used to form said high strength casing ca be at least about 2 times stronger, at least 2 times more rigid, or combinations thereof than a material used to form said chamber. The chamber can fill at least about 70% of a volume of said chamber cavity when said chamber is positioned in said chamber cavity. The chamber can be spaced from an inner surface of said chamber cavity a maximum distance of about 0.001-0.5 inches when said chamber is positioned in said chamber cavity. An outer surface of said chamber can be spaced from an inner surface of said chamber cavity a maximum distance of about 0.001-0.5 inches when said chamber is positioned in said chamber cavity. The bag can fill at least about 70% of a volume of said cavity of said chamber when said bag is positioned in said cavity of said chamber. The high-strength casing can include a plurality of strengthening ribs that form a honeycomb structure on an outside of said high-strength casing. The high-strength casing can include connecting flanges to releasably join together a plurality of parts of said high-strength casing, at least one of said connecting flanges includes a fastening element that releasably connects to another connecting flange. The high-strength casing can include at least one end-to-end inlet channel, at least one end of said end-to-end inlet channel is designed to connect to at least one end of an end-to-end inlet channel that is located on a second high-strength casing to enable a plurality of high-strength casings to be fluidly connected together and to be supplied by a single gas source that includes said gas system. The high-strength casing can include at least one drainage or release valve designed to release gas from the chamber. The high-strength casing can include at least one projection on an exterior surface designed to engage an outer surface of another high-strength casing so as to orient, connect, or combinations thereof the two high-strength casing when positioned together.

The invention is also directed to a device that can be used to store blood, blood products, or combinations thereof that may or may not be under pressure comprising a) a chamber having a cavity, said chamber including first and second chamber parts that form said cavity when releasably connected together, said cavity designed to receive at least one bag that contains the blood, blood products, or combinations thereof; and, b) a high-strength casing and includes a chamber cavity, said high-strength casing including first and second casing parts that form said chamber cavity when releasably connected together, said chamber cavity designed to receive said chamber. The chamber can be a hermetically-sealable cavity. The chamber cavity can be a hermetically-sealable cavity. The chamber can include an inlet channel that fluidly connects said cavity to a casing channel in said high-strength casing to enable a gas source that includes a gas system to be connected to said high-strength casing such that said gas system can flow through said high-strength casing and into said cavity of said chamber. The inlet channel can be hermetically-sealed to said casing channel when said chamber is positioned in said chamber cavity and said first and second parts of said high-strength casing are connected together. The material used to form said high-strength casing can be at least about 2 times stronger, at least 2 times more rigid, or combinations thereof than a material used to form said chamber. The chamber can fill at least about 70% of a volume of said chamber cavity when said chamber is positioned in said chamber cavity. The outer surface of said chamber can be spaced from an inner surface of said chamber cavity a maximum distance of about 0.001-0.5 inches when said chamber is positioned in said chamber cavity. The bag can fill at least about 70% of a volume of said cavity of said chamber when said bag is positioned in said cavity of said chamber. The high-strength casing can include a plurality of strengthening ribs that form a honeycomb structure on an outside of said high-strength casing. The high-strength casing can include connecting flanges to releasably join together a plurality of parts of said high-strength casing, at least one of said connecting flanges includes a fastening element that releasably connects to another connecting flange. The high-strength casing can include at least one end-to-end inlet channel, at least one end of said end-to-end inlet channel is designed to connect to at least one end of an end-to-end inlet channel that is located on a second high-strength casing to enable a plurality of high-strength casings to be fluidly connected together and to be supplied by a single gas source that includes said gas system. The high-strength casing can include at least one drainage or release valve designed to release gas from the chamber. The high-strength casing can include at least one projection on an exterior surface designed to engage an outer surface of another high-strength casing so as to orient, connect, or combinations thereof the two high-strength casing when positioned together.

It is one non-limiting object of the present invention to provide a method for improved platelet concentrate storage.

It is another and/or alternative non-limiting object of the present invention to provide a method for storing platelet concentrate and to minimize the formation of aggregates of platelets during the storage of the platelet concentrate.

It is still another and/or alternative non-limiting object of the present invention to provide a method for storing platelet concentrate and to easily disintegrate any aggregates of platelets that form during the storage of the platelet concentrate.

It is yet another and/or alternative non-limiting object of the present invention to provide a storage container for a bag for the storage of the platelet concentrate.

It is still yet another and/or alternative non-limiting object of the present invention to provide a storage container for a bag having an improved configuration that minimizes the formation of aggregates of platelets during the storage of the platelet concentrate in the bag.

It is another and/or alternative non-limiting object of the invention to provide an improved device for preserving blood products wherein the device forms an all-purpose, reliable, easy-to-manufacture and/or easy-to-use device that can be used in the preservation of blood and/or blood components.

It is yet another and/or alternative non-limiting object of the invention to provide an improved device for preserving blood products that includes two components, namely a chamber that can be hermetically-sealed and high-strength casing that is designed to partially or fully receive the chamber.

It is still another and/or alternative non-limiting object of the invention to provide an improved device for preserving blood products wherein the chamber and/or the high-strength casing can be formed of one or more parts.

It is still another and/or alternative non-limiting object of the invention to provide an improved device for preserving blood products wherein the cavity in the chamber is an airtight cavity.

It is yet another and/or alternative non-limiting object of the invention to provide an improved device for preserving blood products wherein the cavity in the chamber is designed to partially or fully accommodate a bag that contains a blood product.

It is yet another and/or alternative non-limiting object of the invention to provide an improved device for preserving blood products wherein the chamber can include an inlet channel that fluidly connects the cavity to the exterior of the chamber, which inlet channel can be used to feed gas into and/or remove gas from the cavity.

It is still yet another and/or alternative non-limiting object of the invention to provide an improved device for preserving blood products wherein the high-strength casing forms a chamber cavity that is formed from one or more pocket in one or more parts of the high-strength casing, and wherein the chamber cavity is designed to fully or partially receive the chamber.

It is another and/or alternative non-limiting object of the invention to provide an improved device for preserving blood products wherein the chamber cavity of the high-strength casing has a size that is sufficient to fully place the chamber into the chamber cavity, and the chamber cavity has a height that forms a minimal gap between the inner surface of the chamber cavity and the outer surface of the chamber when the chamber is inserted into the chamber cavity.

It is still another and/or alternative non-limiting object of the invention to provide an improved device for preserving blood products wherein the chamber and the high-strength casing perform different functions, wherein the chamber is designed to contact a bag that includes a blood product and the high-strength casing is designed to withstand large forces such that the high-strength casing inhibits or prevents significant deformation and damage to the chamber during the introduction, maintaining and removal of gas in the chamber.

It is yet another and/or alternative non-limiting object of the invention to provide an improved device for preserving blood products wherein the high-strength casing is designed to be a reusable unit and/or the chamber is designed to be disposable.

It is still yet another and/or alternative non-limiting object of the invention to provide an improved device for preserving blood products wherein the size and shape of the cavity of the chamber closely or exactly matches the size and shape of the bag with blood product that is to be placed in the cavity.

It is another and/or alternative non-limiting object of the invention to provide an improved device for preserving blood products wherein the chamber is designed to form a hermetically-sealed cavity.

It is still another and/or alternative non-limiting object of the invention to provide an improved device for preserving blood products wherein the high-strength casing can be embodied as a honeycomb structure produced by strengthening ribs oriented in one or more planes so as to allow for the reduction of weight and the material needed for manufacturing the high-strength casing and still achieve the desired strength and durability of the high-strength casing.

It is yet another and/or alternative non-limiting object of the invention to provide an improved device for preserving blood products wherein the high-strength casing can include connecting flanges to ensure reliable joining of the parts of the high-strength casing.

It is still yet another and/or alternative non-limiting object of the invention to provide an improved device for preserving blood products wherein the flanges on the high-strength casing can include fastening elements.

It is another and/or alternative non-limiting object of the invention to provide an improved device for preserving blood products wherein the high-strength casing can include a fitting that provides fluid communication with the chamber.

It is still another and/or alternative non-limiting object of the invention to provide an improved device for preserving blood products wherein the high-strength casing can include a fitting that provides fluid communication with the chamber and can be designed so as to be positioned in such a way that when the chamber is positioned in the chamber cavity, the fitting is fluidly connected to the inlet channel that fluidly connects the cavity of the camber to the exterior of the chamber.

It is yet another and/or alternative non-limiting object of the invention to provide an improved device for preserving blood products wherein the high-strength casing can include an end-to-end inlet channel that is located on one or more parts of the high-strength casing.

It is still yet another and/or alternative non-limiting object of the invention to provide an improved device for preserving blood products wherein the high-strength casing can include a side channel that abuts to the end-to-end channel, and the side channel is designed to be oriented in the direction of the chamber cavity and terminate at a location where the inlet channel in the high-strength casing is connected.

It is another and/or alternative non-limiting object of the invention to provide an improved device for preserving blood products wherein the high-strength casing can include end fittings to be used to form a fluid connection with another device for preserving blood products.

It is still another and/or alternative non-limiting object of the invention to provide an improved device for preserving blood products wherein a plurality of devices can be stacked together and/or fluidly connected together.

It is yet another and/or alternative non-limiting object of the invention to provide an improved device for preserving blood products wherein the high-strength casing can include a drainage or release valve in which the end-to-end inlet channel is arranged so as to release gas from the chamber.

It is still yet another and/or alternative non-limiting object of the invention to provide an improved device for preserving blood products wherein the high-strength casing includes projections on the external side or outer surface of the high-strength casing so as to assemble together several devices for preserving blood products in a stack configuration.

These and other objects and advantages will become apparent from the following description taken together with the accompanying drawings.

BRIEF DESCRIPTION OF THE DRAWINGS

Reference may now be made to the drawings, which illustrate several non-limiting embodiments that the invention may take in physical form and in certain parts and arrangements of parts wherein.

DETAILED DESCRIPTION OF NON-LIMITING EMBODIMENTS

Figure 1:
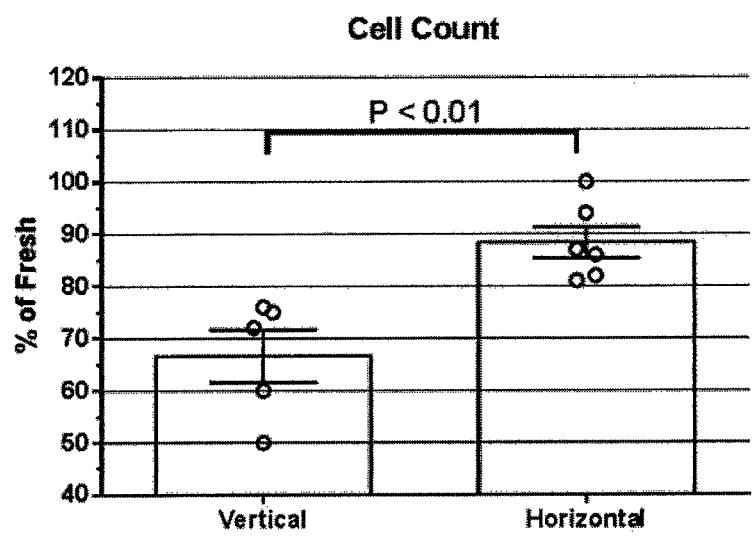
FIG. 1 illustrates comparative data characterizing platelet level of aggregation (as percentage of the initial number of platelets) when preserving and storing platelets in accordance with the present invention.

Referring now to the drawings wherein the showings are for the purpose of illustrating non-limiting embodiments of the invention only and not for the purpose of limiting same, FIGS. 3-12 illustrate several non-limiting platelet concentrate preservation devices 1 that can be used for platelet concentrate preservation in accordance with the present invention.

Figure 3:
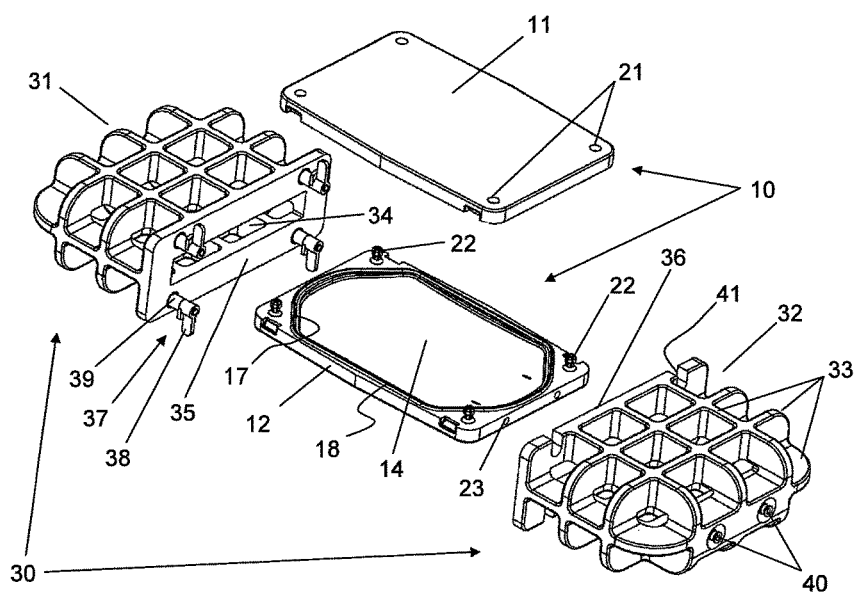
FIG. 3 illustrates an exploded view of one non-limiting blood product preservation device in accordance with the present invention.
Figure 4:
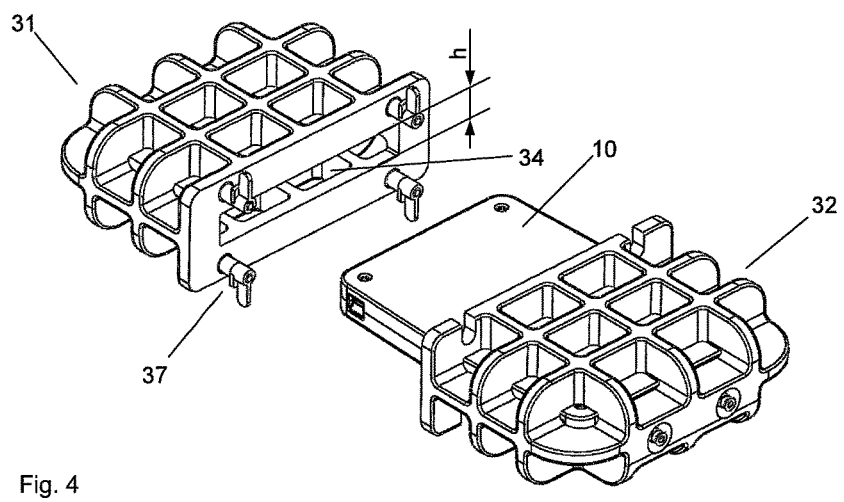
FIG. 4 illustrates a front elevation view of the device shown in FIG. 3, wherein the hermetically-sealed chamber is in the assembled state and inserted into one of the parts of the high-strength casing.
Figure 5:
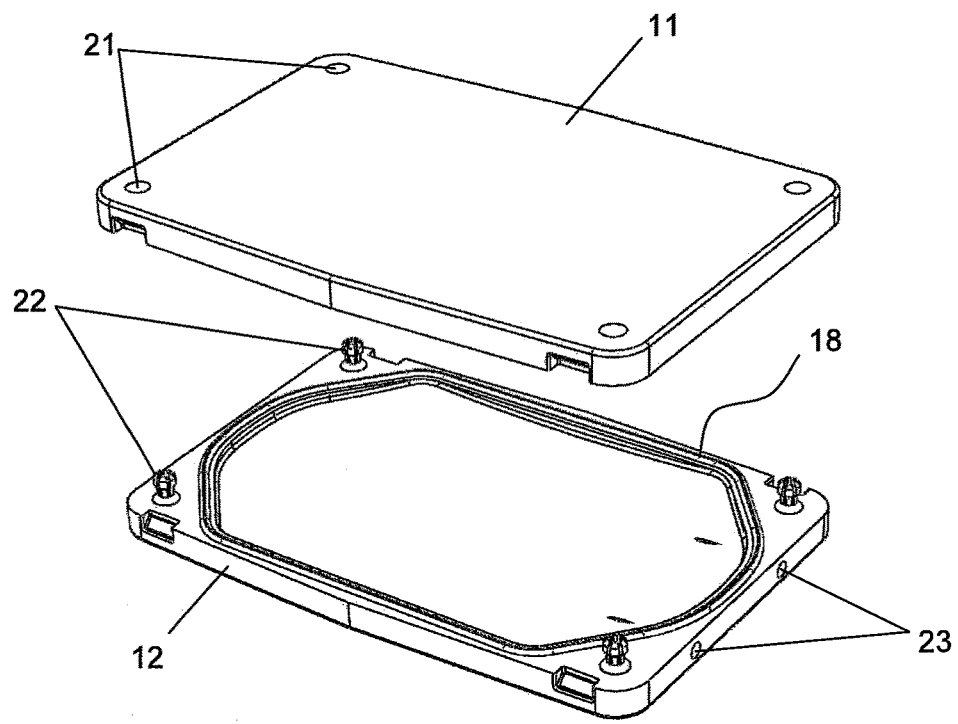
FIG. 5 illustrates a front elevation view of the hermetically-sealed chamber as two individual parts.

As illustrated in FIGS. 3-5, the device 1 includes a hermetically-sealed chamber 10 and a high-strength casing 30. The hermetically-sealed chamber 10 is designed to accommodate a bag with blood and/or a blood product (not shown in FIG. 3). The high-strength casing 30 is designed to protect the hermetically-sealed chamber 10, when located in the high-strength casing, against damage after a gas (e.g., gas or gas mixture) is fed under pressure into the hermetically-sealed chamber. Such a distribution of functions between the two components of device 1 allows the hermetically-sealed chamber 10 to be formed of a thin material (without special requirements to its strength), thus designing the hermetically-sealed chamber as a relatively inexpensive, single use component. The high-strength casing, on the other hand, is designed to be a reusable component of device 1.

As illustrated in FIGS. 3, 5, 7 and 8, the hermetically-sealed chamber 10 includes two parts 11 and 12. The parts are designed to be essentially flat; however, this is not required. Parts 11 and 12 are illustrated as having recesses 13 and 14, respectively, in their central areas. When parts 11 and 12 are joined together, these recesses form a cavity 15, into which a bag with blood product (not shown) is placed. Taking the shape of standard bags for blood products into account (which is close to rectangular in a plan view), the cavity of the hermetically-sealed chamber 10 can be generally shaped as essentially parallelepiped, wherein the legs of which are characterized by proportions close to those characterizing sides of the bag filled with the blood product; however, the cavity can have other shapes.

Figure 8:
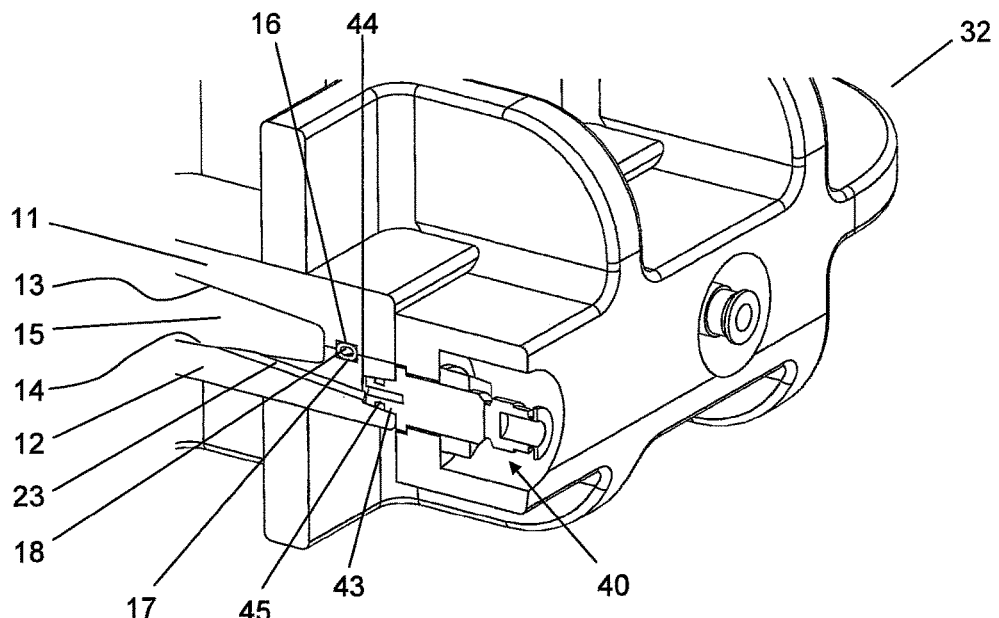
FIG. 8 illustrates an enlarged sectional cross-sectional view of the assembled device illustrated in FIG. 3.

Referring now to FIG. 8, the hermetically-sealed chamber 10 can include annular grooves 16 and 17 that are located along the perimeter of parts 11 and 12 and which groove are positioned on the side of recesses 13 and 14. When parts 11 and 12 are joined together, grooves 16 and 17 form an annular channel, into which a sealing gasket 18 can be position. The sealing gasket can have a variety of shapes. The groove can also have a variety of shapes and sizes. As can be appreciated, only one of the parts can include a groove. The sealing gasket can be in the form of a ring made of flexible material (e.g., rubber, polymer material, silicon, etc.). When parts 11 and 12 are joined-together, gasket 18 provides hermetic sealing of cavity 15.

Figure 6:
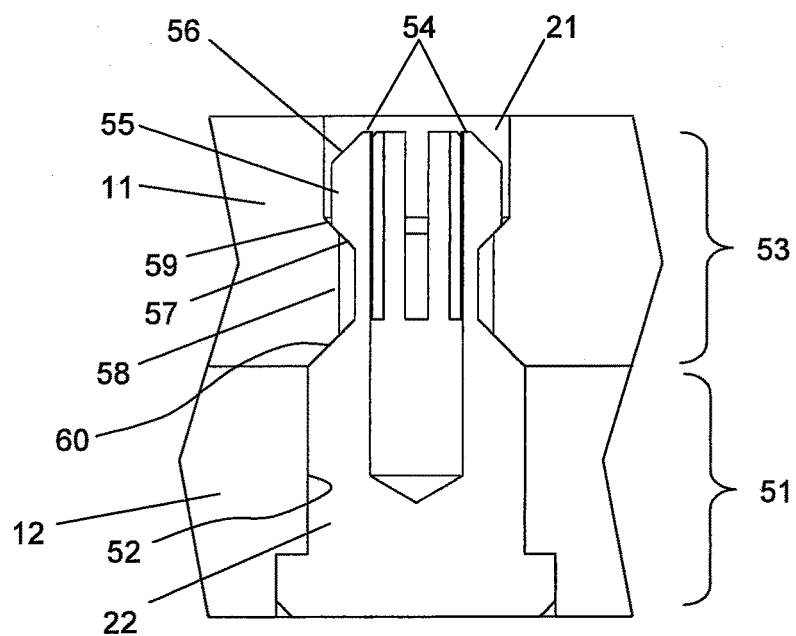
FIG. 6 is an enlarged cross-sectional view of a point of joining of two parts of the hermetically-sealed chamber.
Figure 7:
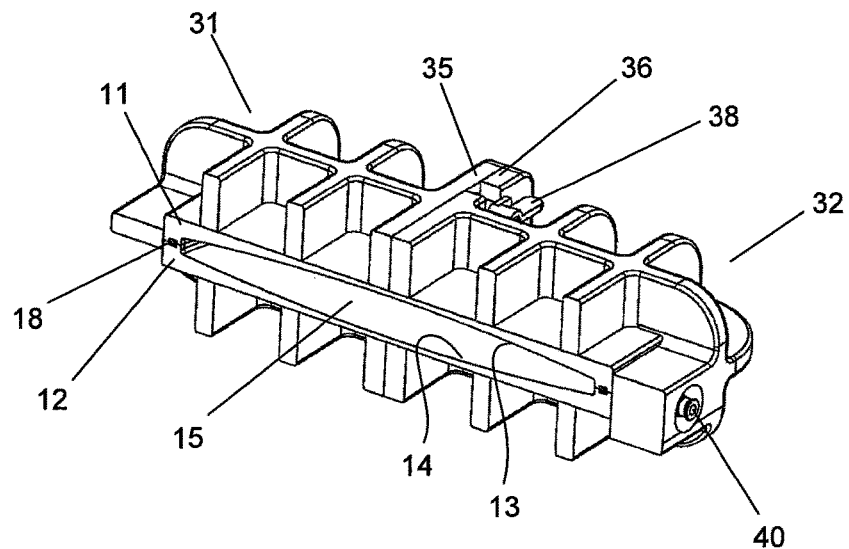
FIG. 7 is a front elevation cross-sectional view of the assembled device illustrated in FIG. 3.

Referring now to FIGS. 3, 5 and 6, parts 11 and 12 of the hermetically-sealed chamber 10 can be held together in the joined-together state by means of four connecting rods 22 installed on parts 12 on the side of recess 14. As can be appreciated, other or additional connection arrangements can be used to hold together parts 11 and 12. As illustrated in FIG. 6, rods 22 can be designed to fit tightly into matched holes 21 made in parts 11. In terms of design, rods 22 and holes 21 can be made so that easy connection/disconnection and reliable holding in place of both parts 11 and 12 of hermetically-sealed chamber 10 in the joined-together state can be achieved. In terms of design, connecting rod 22 can optionally include two parts-cylindrically-shaped base part 51 that is press-fitted or otherwise fixed in opening 52 of part 12 of hermetically-sealed chamber 10 and locking part 53 in the form of a sleeve made of flexible material and cut along its axis. As illustrated in FIG. 6, leaflets 54 (e.g., four leaflets 54) can include projections 55 with two conical surfaces 56 and 57 on their free ends. When parts 11 and 12 of hermetically-sealed chamber 10 are joined together, locking part 53 of connecting rod 22 advances into opening 21 made in part 11 of hermetically-sealed chamber 10. The ring-shaped protrusion 58 with conical surfaces 59 and 60 can be made in the wall of opening 21. In the process of the advancement of rod 22 into opening 21, projections 55 of leaflets 54 slide with their conical surface 56 over conical surface 60 of protrusion 58 of opening 21, and are bent (due to the flexible properties of the material in the direction of axis) and slide further over protrusion 58. On reaching the end of protrusion 58 of opening 21, projections 55 of leaflets 54 slide with their conical surface 57 over conical surface 59 of protrusion 58 and thereafter leaflets 54 unbend and get engaged with their projection 55 with ring-shaped protrusion 58 of opening 21. The size and location of projection 55, leaflets 54 and ring-shaped protrusion 58 are selected so that their mutual engagement takes place in the end position of parts 11 and 12 of hermetically-sealed chamber 10 that are being joined together. As a result, the above-described joint ensures reliable holding in place of parts 11 and 12 of hermetically-sealed chamber 10 in the joined-together state, and the sealing gasket 18 provides hermetic sealing of the joint. Due to the flexibility of leaflets 54 and conical surfaces of projections 55 and protrusions 58, the described design of the joint (e.g., connecting rod 22 and opening 21) ensures not only easy connection of parts 11 and 12, but also easy disconnection. As can be appreciated, other designs ensuring connection of parts 11 and 12 of hermetically-sealed chamber 10 can be used.

Both parts 11 and 12 of hermetically-sealed chamber 10 plus connecting rods 22 can be made, for example, out of plastic using injection molding methods or another method with selection of suitable materials providing required rigidity of produced articles and flexible properties of locking part 53 of connecting rods 22. As can be appreciated, other or additional materials can be used to form hermetically-sealed chamber 10. As illustrated in FIG. 8, at least one channel 23 and a cavity 15 is formed when parts 11 and 12 are joined together.

Referring now to FIGS. 3 and 4, high-strength casing 30 is formed of two parts 31 and 32 that are designed to be joined together. Each part 31 and 32 of high-strength casing 30 is embodied as a honeycomb structure having strengthening ribs 33 oriented in three orthogonal planes and each forming pocket 34 in the central area. As can be appreciated, the number and orientation of the strengthening ribs on parts 31 and 32 are non-limiting. As also can be appreciated, parts 31 and/or 32 can be absent strengthening ribs and/or other structures can be included in and/or used on parts 31 and/or 32 to provide structural strength to one or both parts. Pocket 34 is designed to accommodate at least a portion of hermetically-sealed chamber 10 when parts 31 and 32 are in the joined-together state. The joining of the two pockets together forms a chamber cavity for chamber 10. The size and depth of pocket 34 is sufficient for the accommodation of at least a portion (e.g., 40-60%, 50%, etc.) of chamber 10 in each part 31 and 32 of high-strength casing 30. The height ("h") of pocket 34 is generally selected to ensure placement of chamber 10 in the pocket with a minimal gap between the inner surface of the pocket and the outer surface of chamber 10.

Each part 31 and 32 of high-strength casing 30 can include a flange 35, 36, respectively, on the open side of pocket 34. Four twist locks 37 can be optionally positioned on flanges 35 of part 31. The twist locks, when used, can include a fixing catch 38 that are secured on bar 39 in such a way that the catch 38 is rotatable. As can be appreciated, the fixing catch can have other configurations. Mating cuts 41 can be formed in flange 36 of part 32. After flange 35 of part 31 and flange 36 of part 32 are joined together, fixing catches 38 can be turned in the direction of pocket 34, after which they turn out to be engaged with the rear part of flange 36. Thus, both parts 31 and 32 of high-strength casing 30 can be reliably fixed in the joined-together state. As can be appreciated, other or additional connection arrangements can be used to releaseably connect together parts 31 and 32. Parts 31 and 32 of high-strength casing 30 can be made, for example, out of plastic (using injection molding method or another method for this purpose) with selection of suitable materials that provide required rigidity and strength of manufactured article and which can protects hermetically-sealed chamber 10 from damage after gas is pumped into it under pressure.

As illustrated in FIG. 8, a fitting 40 can be used to fluidly connect the inner space of part 31 and/or 32 (that forms a part of the chamber cavity that is intended for accommodating a portion of the hermetically-sealed chamber 10). The fitting can be installed on the end face of part 31 and/or 32 of high-strength casing 30. Fitting 40 is positioned in such a way that when hermetically-sealed chamber 10 is placed into pocket 34 of part 31 and/or 32, fitting 40 gets hermetically connected with the inlet channel 23 made in the end face of part 12 of hermetically-sealed chamber 10. For this purpose, fitting 40 has a projecting part 43 on its inner side, and the projecting part 43 advances into recess 44 made in the end face of part 12 of hermetically-sealed chamber 10 and connects with inlet channel 23. Hermetic sealing of the connection can be provided by means of a sealing ring 45 installed in the annular groove made on the side surface of projecting part 43. As can be appreciated, other or additional arrangements can be used ensuring hermetic sealing of the joint between inlet channel made in the end face of part 12 of hermetically-sealed chamber 10 and fitting 40 that is installed in the end face of part 31 and/or 32 of high-strength casing 30. The seal between inlet channel 23 and fitting 40 can be formed prior to or when parts 31 and 32 are connected together.

After the hermetically-sealed chamber 10 is placed into the chamber cavity of the high-strength casing 30, cavity 15 of chamber 10 is can be designed to be fluidly connected to the outside of casing 30 via channel 23 and fitting 40; however, this is not required. Also, a one-way valve (not shown) can optionally be installed in fitting 40, which, on the one hand, allows insertion of a gas into cavity 15 of hermetically-sealed chamber 10 and, on the other hand, can be used to prevent gas egress from cavity 15.

Figure 9:
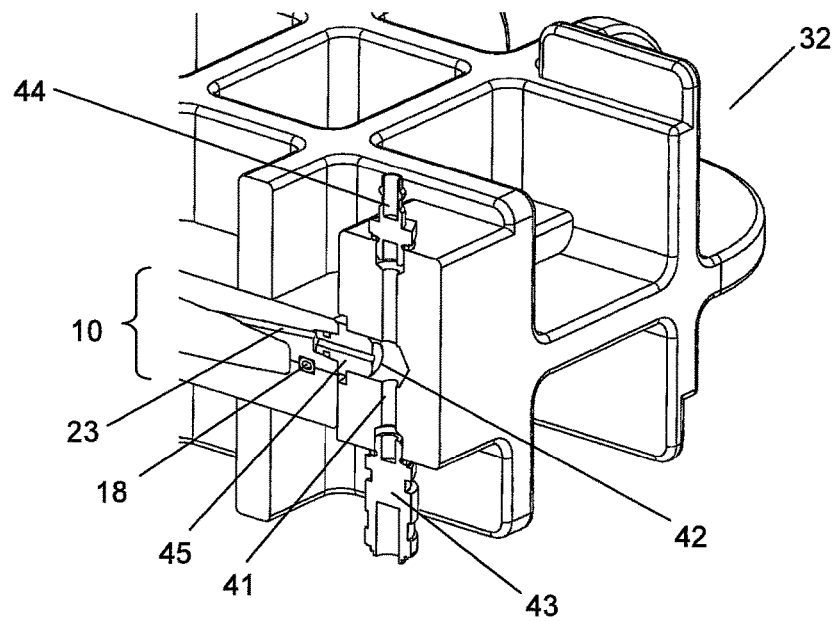
FIG. 9 illustrates an enlarged sectional cross-sectional view of the assembled device illustrated in FIG. 3.

Referring now to FIGS. 9-12, another non-limiting embodiment of the device in accordance with the present invention is illustrated. In contrast to the embodiment of the device illustrated in FIGS. 3-8, the device illustrated in FIGS. 9-12 is characterized by another design solution for components that provide feeding of a gas into cavity 15 of hermetically-sealed chamber 10, which is capable of feeding gas concurrently into a plurality of devices 10 that are arranged in a stack configuration. Referring now to FIG. 9, an end-to-end inlet channel 41 is made in part 31 and/or 32 of high-strength casing 30. The channel can be oriented generally perpendicular to the horizontal plane of the device; however, this is not required. A side channel 42 can be designed to abut the end-to-end channel 41, wherein the side channel 42 is designed to go in the direction of pocket 34 of part 21 and/or 32 so as to be able to engage with to inlet channel 23 of hermetically-sealed chamber 10, as previously described above, when chamber 10 is placed the of chamber cavity of the high-strength casing 30. End fitting 43 can be installed on one end of end-to-end inlet channel 41, and end fitting 44 can be installed on the other end of end-to-end inlet channel 41. End fittings 43 and 44 can optionally include a built-in one-way valve, not shown, through which gas can be fed into the device. Fitting 45 can be installed inside channel 42; however, this is not required. Fitting 45 can be designed to ensure airtight joining with hermetically-sealed chamber 10. This airtight joint is embodied in a similar way as the connection between fitting 40 and hermetically-sealed chamber 10 that is illustrated in FIG. 6. As such, once hermetically-sealed chamber 10 is placed into the chamber cavity of high-strength casing 30, an airtight cavity 15 of hermetically-sealed chamber 10 can be connected (through inlet channel 23 and fitting 45) with end-to-end inlet channel 41, into which gas can fed through fittings 43 or 44.

Figure 12:
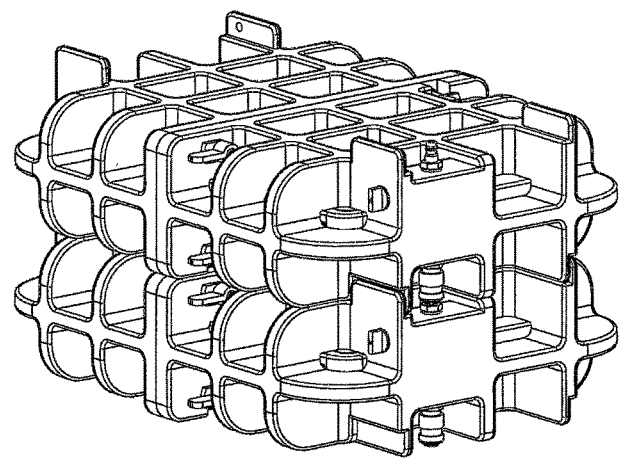

Fittings 43 and 44 can optionally be made as quick-disconnect couplings, and fitting 43 of one device can be designed in such a way that airtight joining with end fitting 44 of another device can be achieved. Such a design provides the opportunity to arrange together several devices 1 in a stack configuration by fluidly connecting them together by means of fittings 43 and 44. As a result, end-to-end inlet channels 41 of devices 1 can be fluidly connected in series, thus forming a single inlet channel, through which gas can be fed concurrently into all the devices as illustrated in FIG. 12.

Figure 10:
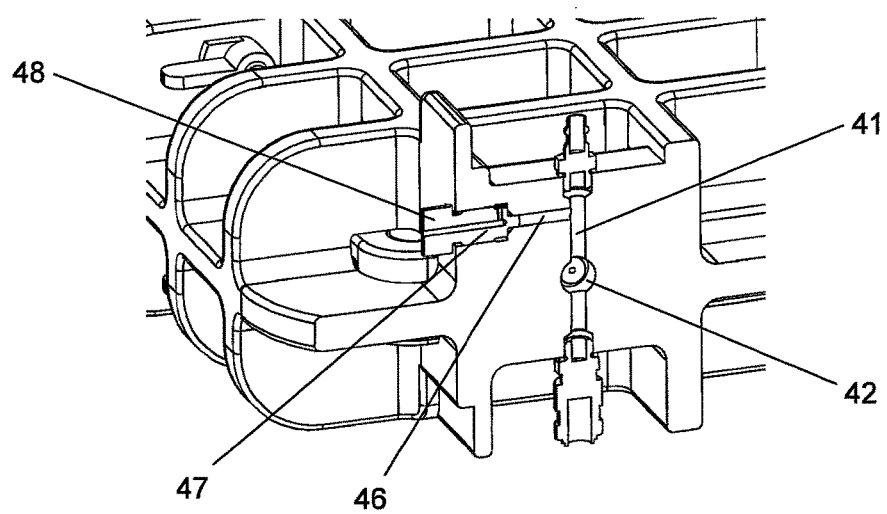
FIG. 10 illustrates an enlarged sectional cross-sectional view of the assembled device illustrated in FIG. 3.

A drainage channel 46 with drainage valve 47 as illustrated in FIG. 10 can optionally be provided. The drainage channel can be included in part 31 and/or 32 of high-strength casing 30. The drainage channel 46 is designed to release gas from hermetically-sealed chamber 10 of the device. Drainage channel 46 can be designed to abut to end-to-end inlet channel 41 and goes outside part 31 and/or 32 of high-strength casing 30, thereby connecting end-to-end inlet channel 41 with the ambient atmosphere. Drainage valve 47 (installed in drainage channel 46) enables the release gas from hermetically-sealed chamber 10 of the device, when necessary or desired. By turning handle 48, drainage valve 47 can be designed to be opened, thus letting the gas to pass from hermetically-sealed chamber 10 of the device into the ambient environment. As can be appreciated, other or additional designs can be used to controllably release gas from hermetically-sealed chamber 10.

Figure 11:
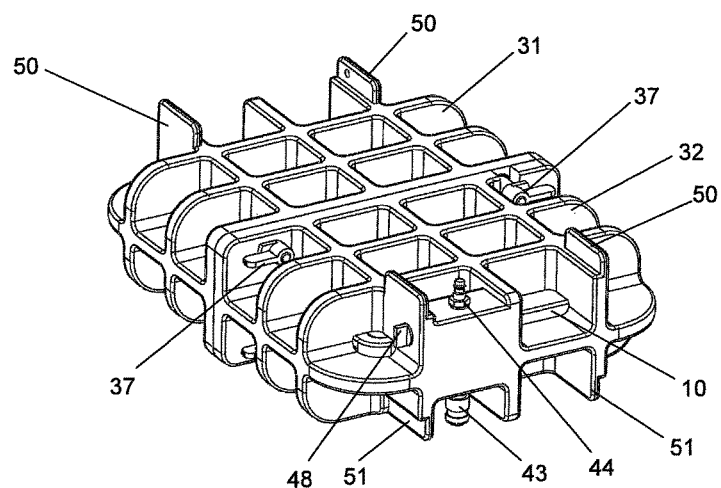
FIG. 11 illustrates a front elevation view of the assembled device of FIGS. 3; and, FIG. 12 illustrates a plurality of assembled devices as illustrated in FIG. 11 in a stacked orientation.

One non-limiting example of a device 1 for preserving and storing blood products according to the present invention is illustrated in FIG. 11. The device is shown in the assembled state and the following device components can be seen: the edge of hermetically-sealed chamber 10 installed into high-strength casing 30, parts 31 and 32 of which are interconnected by means of twist locks 37, fittings 43 and 44 intended for feeding gas into device and handle 48 of drainage valve intended for gas release.

Additionally, parts 31 and 32 of the high-strength casing can optionally have projections 50 and 51 oriented in the opposite directions relative to the horizontal plane of the device. Projections 50 and 51, when used, are intended for arranging several devices 1 in a stack as illustrated in FIG. 12. Projections 50 can be shifted in the horizontal plane relative to the lying-opposite projections 51 in such a way that when arranging several devices in a stack, projections 50 of a device interact with projections 51 of the device located above the first one, and, accordingly, projections 51 interact with projections 50 of device located below the first one. Projection 51 is illustrated as having a recess portion that is designed to frictionally engage a portion of projection 50 when the devices are stacked together. Due to such an approach, projections 50 and 51 keep the stacked devices in place as shown in FIG. 12. Additionally, projections 50 and 51 can optionally be equipped with fasteners (e.g., screws, clamps, clips, etc.) not shown, which can be used to releasable secure together a plurality of stacked devices 1 to provide higher reliability of connecting together the stacked-together devices. This can be advantageous when a plurality of stacked devices are to be transported. As can be appreciated, other or additional configurations can be used to ensure in the releasably connecting together of several stacked devices.

The above-described device can be used to preserve and store blood products that use a method wherein the preservation and storage takes place in a gas medium, including the situation where the method takes place under conditions of increased pressure. For instance, the device of the present invention can be used when implementing blood product preservation methods described in US 2010/0009334.

In accordance with the present invention, the device can function as follows:

A blood product (e.g., platelet concentrate, whole blood, packed red blood cells) is placed in a bag made of gas-permeable material. Depending on the gas used (a pure gas, a gas mixture composition), a material used for bag manufacturing should be characterized by adequate gas permeability. Specifically, when implementing the preservation method which involves the use of xenon, a bag material should be permeable for xenon. For instance, bags for platelet concentrate storage produced by CardianBCT (Lakewood, Colo.) and characterized by the above-indicated gas-permeability feature can be used for this purpose. Blood products to be preserved can be obtained through the use of well-known methods and appropriate available equipment.

The hermetically-sealed bag with the blood product is placed in cavity 15 that is formed as a result of joining together parts 11 and 12 of hermetically-sealed chamber 10. An easy-to-use and reliable joining arrangement of parts 11 and 12 of hermetically-sealed chamber 10 can be used as above-described, wherein openings 21 are made in part 11 and connecting rods 22 are installed on part 12 of hermetically-sealed chamber 10. After the joining together of parts 11 and 12 (using sealing gasket 18 for this purpose), the bag with blood product is positioned in cavity 15 of hermetically-sealed chamber 10. The cavity 15 is connected with the outside only by means of inlet channel 23. Thereafter, parts 31 and 32 of high-strength casing 30 are inserted about hermetically-sealed chamber 10 to thereby position chamber 10 in the chamber cavity of the high-strength casing 30, which chamber cavity is formed by the joining together of pockets 34 of parts 31 and 32. The fixing catches 38 of twist locks 37, when used, are turned in advance in the opposite direction from pocket 34. Parts 31 and 32 are joined together when flanges 35 and 36 are fit tightly together and thereafter fixing catches 38 of twist locks 37 are turned, thus releasably connecting together parts 31 and 32. Fitting 42 is designed to connect hermetically with channel 23 of hermetically-sealed chamber 10, as a result of which cavity 15 of hermetically-sealed chamber 10 (after the latter has been placed into high-strength casing 30) turns out to be connected with the outside only through channel 23 and fitting 40. As described above, the one-way valve installed in fitting 40 provides unidirectional passage of gas into cavity 15 of hermetically-sealed chamber 10. Pockets 34 of parts 31 and 32 are also designed to be hermetically joined when parts 31 and 32 are connected together.

The gas that is required in compliance with the used preservation method is then fed (e.g., under pressure) into cavity 15 of hermetically-sealed chamber 10 through fitting 40. The gas is fed until the pressure in cavity 15 reaches a required value, after which gas feeding is terminated and the device is disconnected from the gas feeding system. The gas feeding system (not shown) may comprise a high-pressure bottle containing gas mixture of a required composition and tubing with a manometer and controlled valve made in such a way that it is possible to connect it hermetically with fitting 40. As can be appreciated, other or additional arrangements of the gas feeding system can be used.

Subsequent actions with the device, into which a bag with blood is placed and gas of required composition is pumped, are determined by a used method for preserving and storing blood products. Specifically, the device in the above-indicated state is kept during a certain period of time sufficient for the blood product to achieve the desired saturation with the appropriate component of gas pumped into the device. After that, the device can be placed for storage at pre-specified temperatures (e.g., into a refrigerator).

For instance, when implementing the method described in US 2010/0009334, a bag with platelet concentrate is first placed in a hermetically-sealed chamber 10, which is then placed in high-strength casing 30, after which a gas feeding system is connected through fitting 40. A gas mixture containing xenon (e.g., at least 50-65% xenon) serves as the gas. Due to the fact that the bags are made of gas-permeable material for xenon, the platelet concentrate (contained in the bags) is saturated with xenon, and creates conditions (namely, composition, pressure exerted by gas mixture and temperature) to provide preservation of the platelet concentrate in the bag. Subsequently, the device is stored in a refrigerator at a temperature approximately from 3° C. to 6° C. It is desirable to place the device in a horizontal position. Taking the geometrical relationship of sides (indicated above) of the hermetically-sealed chamber and the device as a whole into account, a bag with blood product is stored in a position to ensure maximum area and minimum thickness of sediment formed in the course of platelet sedimentation during storage. However, if necessary, the blood product can be stored at a different orientation in the device.

Prior to using the preserved blood product, the device is taken out from the refrigerator. If necessary, prior to unsealing the device, it can optionally be placed on a shaker for stirring the blood product contained in the bag. A sediment of formed elements of blood (produced in the course of storage) can then be transformed into the suspension as a result of stirring, while the increased pressure maintained during stirring inhibits or prevents generation of gas bubbles in the blood product.

Thereafter, the gas is released from the hermetically-sealed chamber 10 (for instance, using a drainage valve for this purpose—as shown in FIG. 10), and after the pressure in cavity 15 is equalized with atmospheric pressure, the hermetically-sealed chamber 10 is opened and the bag with blood product is taken out from the chamber. Prior to using the blood product, the bag can be kept for a certain time period until it warms up naturally (e.g., to room temperature) and the gas pressure inside the bag equalizes with atmospheric pressure.

Another non-limiting method for a platelet concentrate preservation method in accordance with the present invention is set forth as follows:

A platelet concentrate (not shown) is placed in a bag made of material that is at least permeable for xenon and oxygen. For example, bags for platelet concentrate storage produced by CardianBCT (Lakewood, Colo.) characterized by the above-indicated gas-permeability feature could be used for this purpose.

The bag containing the platelet concentrate is hermetically-sealed.

The hermetically-sealed bag with platelet concentrate is placed in cavity 15 formed as a result of joining together parts 11 and 12 of chamber 10. After joining parts 11 and 12 together, the bag with the platelet concentrate (not shown in FIGS. 3 and 4) is positioned in chamber 10 (e.g., the chamber is hermetically-sealed) and the inner space of cavity 15 is fluidly connected with channel 23.

Parts 31 and 32 of high-strength casing 30 are inserted about chamber 10 and are connected together (e.g., with fixing catches 38 of twist locks 37 being turned in advance in the opposite direction from opening 34). Parts 31 and 32 are joined together to the point when flanges 35 and 36 fit tightly, after which fixing catches 38 of twist locks 37 are rotated, thus fixing parts 31 and 32 in the joined-together state. In this process, fitting 42 gets connected hermetically with channel 23 of hermetically-sealed chamber 10. As such, cavity 15 of chamber 10 is fluidly connected to channel 23 and fitting 42 to enable gas to be inserted and/or removed from chamber 10 via channel 23 and filling 42. A valve (e.g., one-way, etc.) can be installed in fitting 42 to provide controlled (e.g., unidirectional, etc.) passage of gas into and/or out of cavity 15 of chamber 10.

After the bag has been placed into the platelet concentrate preservation device, a gas mixture with xenon, xenon and oxygen (e.g., 79-95% xenon and 5-21% oxygen), or xenon and one or more other gasses (e.g., air, oxygen, nitrogen, etc.) is pumped (e.g., under pressure) into cavity 15 of chamber 10 via channel 23 and fitting 42. The gas mixture is fed until the pressure in cavity 15 reaches a desired value (e.g., 3.5-5 bars above atmospheric pressure, etc.), after which the device is disconnected from the gas source. The system for feeding the gas mixture (not shown) may include a high-pressure bottle containing the gas mixture and tubing with a manometer and a controlled valve that is made in such a way that it is possible to connect it hermetically with fitting 42. As can be appreciated, other or additional arrangements for the system for feeding the gas mixture can be used.

The step of feeding the gas mixture to chamber 10 can be carried out at a temperature of ambient environment and the gas mixture having a temperature of about 20° C. to 24° C.; however, other temperatures can be used.

The platelet concentrate preservation device, after being fed the gas mixture, is generally kept in the above-described state for a time period sufficient for partial or full saturation of the platelets with xenon. To reduce this time period and to ensure a higher-degree saturation of the platelets with xenon, the platelet concentrate can optionally be additionally stirred (e.g., placing the device on a shaker [i.e., a standard shaker for platelet concentrate storage could be used for this purpose], etc.).

The platelet concentrate preservation device, after desired xenon saturation of the platelet concentrate is obtained, can be placed in a refrigerator, in which it is stored at a desired temperature (e.g., 3° C. to 6° C.). A standard refrigerator that is conventionally used for storing blood components can be used for this purpose. Due to the fact that the bags are made of a gas-permeable material, the platelet concentrate (contained in the bags) is partially or fully saturated with xenon, and creates conditions (namely, composition, pressure exerted by gas mixture and temperature) that provide for the preservation of platelet concentrate in the bag. The platelet concentrate preservation device can be stored in the refrigerator with the bag being in the generally horizontal position.

Prior to using the preserved platelet concentrate, the platelet concentrate preservation device is taken out of the refrigerator and optionally placed on a shaker for stirring. The platelet pellet that has formed during the storage period is transformed (e.g., broken up, etc.) as a result of stirring, and the increased pressure maintained in the course of stirring inhibits or prevents generation of gas bubbles in the platelet concentrate. After the optional shaking or stirring step, the valve in fitting 42 is opened and any excess pressure is released from cavity 15. Thereafter, chamber 10 is opened and the bag with platelet concentrate is removed from chamber 10. Prior to using the platelet concentrate, the bag is held for a certain time period to enable the bag to warm up (e.g., naturally warm to room temperature) and to allow the gas pressure inside the bag to equalize with atmospheric or ambient pressure.

Another non-limiting method for a platelet concentrate preservation method in accordance with the present invention is set forth as follows:

A platelet concentrate (not shown) is placed in a bag made of material that is at least permeable for xenon and oxygen. For example, bags for platelet concentrate storage produced by CardianBCT (Lakewood, Colo.) characterized by the above-indicated gas-permeability feature could be used for this purpose.

The bag containing the platelet concentrate is hermetically sealed.

The hermetically-sealed bag with platelet concentrate is placed in cavity 15 formed as a result of joining together parts 11 and 12 of chamber 10. After joining parts 11 and 12 together, the bag with the platelet concentrate (not shown in FIGS. 3-12) is positioned in chamber 10 (e.g., the chamber is hermetically sealed) and the inner space of cavity 15 is fluidly connected with channel 23.

Parts 31 and 32 of high-strength casing 30 are inserted about chamber 10 and are connected together (e.g., with fixing catches 38 of twist locks 37 being turned in advance in the opposite direction from opening 34). Parts 31 and 32 are joined together to the point when flanges 35 and 36 fit tightly, after which fixing catches 38 of twist locks 37 are rotated, thus fixing parts 31 and 32 in the joined-together state. In this process, fitting 42 gets connected hermetically with channel 23 of hermetically-sealed chamber 10. As such, cavity 15 of chamber 10 is fluidly connected to channel 23 and fitting 42 to enable gas to be inserted and/or removed from chamber 10 via channel 23 and filling 42. A valve (e.g., one-way, etc.) can be installed in fitting 42 to provide controlled (e.g., unidirectional, etc.) passage of gas into and/or out of cavity 15 of chamber 10.

After the bag has been placed into the platelet concentrate preservation device, a gas mixture with xenon and oxygen (e.g., 79-95% xenon and 5-21% oxygen) is pumped (e.g., under pressure) into cavity 15 of chamber 10 via channel 23 and fitting 42. The gas mixture is fed until the pressure in cavity 15 reaches a desired value (e.g., 3.5-5 bars. etc.), after which the device is disconnected from the gas source. The system for feeding the gas mixture (not shown) may include a high-pressure bottle containing the gas mixture and tubing with a manometer and a controlled valve that is made in such a way that it is possible to connect it hermetically with fitting 42. As can be appreciated, other or additional arrangements for the system for feeding the gas mixture can be used.

The step of feeding the gas mixture to chamber 10 can be carried out at a temperature of ambient environment and the gas mixture having a temperature of about 20° C. to 24° C.; however, other temperatures can be used.

The platelet concentrate preservation device, after being fed the gas mixture, is generally kept in the above-described state for a time period sufficient for partial or full saturation of the platelets with xenon. To reduce this time period and to ensure a higher-degree saturation of the platelets with xenon, the platelet concentrate can optionally be additionally stirred (e.g., placing the device on a shaker [i.e., a standard shaker for platelet concentrate storage could be used for this purpose], etc.).

The platelet concentrate preservation device, after desired xenon saturation of the platelet concentrate is obtained, can be placed in a refrigerator, in which it is stored at a desired temperature (e.g., 3° C. to 6° C.). A standard refrigerator that is conventionally used for storing blood components can be used for this purpose. Due to the fact that the bags are made of a gas-permeable material, the platelet concentrate (contained in the bags) is partially or fully saturated with xenon, and creates conditions (namely, composition, pressure exerted by gas mixture and temperature) that provide for the preservation of platelet concentrate in the bag. The platelet concentrate preservation device can be stored in the refrigerator with the bag being in the generally horizontal position.

Prior to using the preserved platelet concentrate, the platelet concentrate preservation device is taken out of the refrigerator and optionally placed on a shaker for stirring. The platelet pellet that has formed during the storage period is transformed (e.g., broken up, etc.) as a result of stirring, and the increased pressure maintained in the course of stirring inhibits or prevents generation of gas bubbles in the platelet concentrate. After the optional shaking or stirring step, the valve in fitting 42 is opened and any excess pressure is released from cavity 15. Thereafter, chamber 10 is opened and the bag with platelet concentrate is removed from chamber 10. Prior to using the platelet concentrate, the bag is held for a certain time period to enable the bag to warm up (e.g., naturally warm to room temperature) and to allow the gas pressure inside the bag to equalize with atmospheric or ambient pressure.

A set of experiments was staged to verify the implementation of the platelet concentrate preservation method according to the present invention and to confirm the obtainment of the above-indicated results as compared to the known methods.

EXPERIMENT 1

The platelet concentrate was placed into plastic bags intended for platelet concentrate storage. The bag with platelet concentrate was placed in the above-described device (see FIGS. 3-12), into which a gas mixture containing 87% xenon and 13% oxygen was pumped under pressure into cavity 15. After keeping the platelet concentrate preservation device a period of 3.5 hours at room temperature (e.g., 22° C.), the platelet concentrate preservation device was placed in a refrigerator (temperature of approximately 4° C.). The platelet concentrate was stored for a period of 14 days.

The platelet concentrate was obtained by the standard method used in clinics—by means of an aphaeresis apparatus, Trima Accel®, with the use of standard bags having gas-permeable walls for platelet concentrate storage. These bags were available from CardianBCT (Lakewood, Colo.). The parameters for obtaining the platelet concentrate were as follows:

a. relationship of blood to anticoagulant when taking blood sample 11:1;

b volume of platelet concentrate in one bag 200-300 ml;
c. platelet concentration—(1 1.5)×10⁹ cells per ml.

To verify the method claimed herein, six (6) experimental bags with platelet concentrate from different donors were used and five (5) control (reference) bags with platelet concentrate from different donors were used. The preservation method described in the method and device for preserving blood or its components in gas medium under pressure and system for same (PCT Application Serial No. PCT/US2012/043449 [WO 2012/177820], which is incorporated herein by reference) was used for the bags of the control (reference) group, and the gas mixture composition in these bags was the one described in the method for preserving platelets in the gas mixture (PCT Application No. PCT/US2012/057211 [WO 2012/049118], which is incorporated herein by reference).

The experimental bags were stored in accordance with the present invention—in a generally horizontal position. Upon completion of storage, the platelet concentrate preservation device with the experimental bags was taken out from the refrigerator and placed on an orbital shaker. Stirring was conducted at room temperature (approximately 22° C.) for a time period of about ten (10) minutes with a rotation frequency of 150 min$^{-1}$ (rpm). After the shaking step, the pressure of the gas mixture was released from cavity 15, and the bag was taken out of the platelet concentrate preservation device and kept for three (3) hours at room temperature (without stirring) to allow the bag to naturally warm up and to allow the pressure in the bag to equalize with the ambient atmosphere at sea level (e.g., 1 atm.).

The control (reference) bags were stored in a vertical position. Upon completion of storage, the storage device that included the control (reference) bag was taken out from the refrigerator and the pressure of the gas mixture was released from the storage device. The extracted bag was then carefully crumpled to eliminate the platelet pellet. Thereafter, the bag was taken out from the storage device and kept for three (3) hours at room temperature (without stirring) to allow the bag to naturally warm up and to allow the pressure in the bag to equalize with the ambient atmosphere at sea level (e.g., 1 atm.).

Counting of the cells and the taking of measurements of the aggregation level of the experimental bags and control bags was used to determine the quality of platelet concentrate to compare the two preservation and storage processes.

Cell Count—a parameter indicating the degree of platelet population preservation after storage. This parameter is calculated as a percentage from the number of cells in the beginning of experiment—i.e., prior to starting the platelet concentrate preservation. A high percentage of preserved cells indicates that a small number of flakes and micro-aggregates were formed during storage as a result of platelets sticking together. The cells were counted before and after storage with the use of Guava EasyCyte 5HT Flow Cytometer—which can directly determine cell concentration in a sample being analyzed.

Aggregation—a functional indicator of cell activity. This measurement indicates the ability of stored platelets to produce clots in blood vessels with damaged walls after transfusion. The platelets' level of aggregation was determined by means of a SOLAR AP-2110 (Belarus) aggregometer by turbidimetric method (Jarvis G E., "Platelet aggregation: turbidimetric measurements" *Methods Mol Biol* 272: 65-76 (2004) with the use of an ADP and an epinephrine as inducing factors for the mixture. This method is used to measure (in percentage terms) the variation in platelet suspension transparency after the addition of an aggregation agent.

Figure 2:
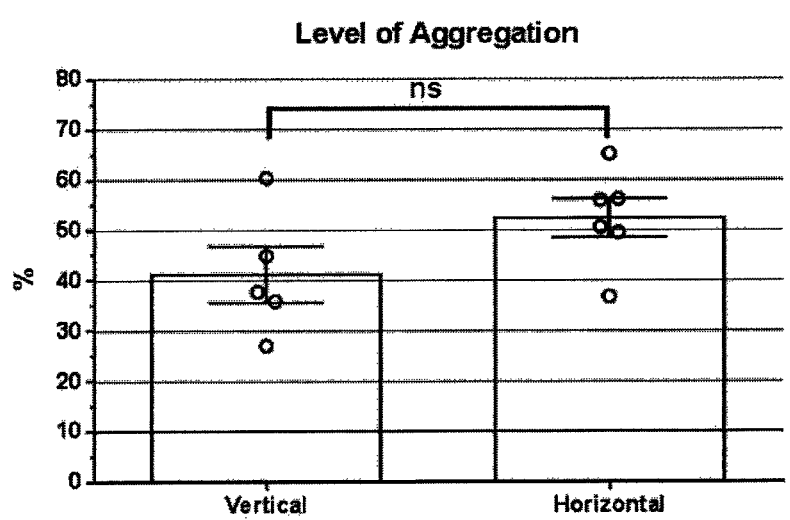
FIG. 2 illustrates comparative data characterizing the degree of platelet preservation (as percentage in relation to the maximum level of aggregation) when preserving and storing platelets in accordance with the present invention.

To obtain data for the above-named parameters, each sample was measured 3-5 times. Measurement results are illustrated in FIGS. 1 and 2 as an arithmetic means. Statistical processing of the results and the graph plotting was performed using a GraphPad Prism2® version 6.01 for Windows, GraphPad Software (La Jolla Calif. USA, www.graphpad.com). Each point on the graphs in FIGS. 1 and 2 corresponds to an arithmetic mean for 3-5 measurements for a specific donor, while the columns give an arithmetic mean for experimental (Horizontal) and control/reference (Vertical) groups of donors. Also, standard error (SEM) is shown in FIGS. 3 and 4. A T-test was used to compare the experimental and control (reference) groups. The difference in the results is shown in the graphs as "P<0.01" (the difference is reliable) or "ns" (the difference is unreliable).

It can be seen from FIG. 1 that the platelet preservation method in accordance with the present invention results in an increased number of preserved platelets by over 20% (on average) as compared to prior art preservation methods. Such a difference is statistically reliable (P=0.0083).

It can be seen from FIG. 1 that the platelet preservation method in accordance with the present invention does not impair the functional properties of platelets. The platelets level of aggregation in the experimental group is higher by over 10% (on average) than that for the control (reference) group, though this difference is considered to be statistically unreliable (P=0.1407).

As such, the method in accordance with the present invention enables one to store platelet concentrate more efficiently, prevent the sticking of platelets together, and not impair the functional properties of the platelets. The aphaeresis platelet concentrate (obtained through the use of standard methods) and standard plastic bags intended for platelet concentrate storage could be used with the method in accordance with the present invention. The absence of dense deposit in the end of storage period allows for improved quality and safety of platelet concentrate that is transfused to patients.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

We claim:
1. A method for platelet concentrate storage comprising:
   a. placing blood, blood components, or combinations thereof in a hermetically-sealed bag, wherein the bag is formed of a material that is permeable to a gas system;

b. placing the bag in a cavity of a chamber, said chamber including first and second chamber parts that form said cavity when connected together;

c. placing said chamber that includes said bag into a chamber cavity of a high-strength casing, said high-strength casing including first and second casing parts that form said chamber cavity when connected together;

d. feeding said gas system into said cavity of said chamber to at least partially saturate said blood, blood components, or combinations thereof with at least one gas in said gas system, said gas system fed to said chamber under pressure that is greater than atmospheric pressure at sea level; and, e. maintaining said bag of said blood, blood components, or combinations in said cavity of said chamber in said presence of said gas system for at least 0.001 hours.

2. The method as defined in claim 1, further including the step of:

f. after said blood, blood components, or combinations thereof have reached a desired saturation of said at least one gas in said gas system, cooling said bag that contains said blood, blood components, or combinations thereof in a cooling system to a storage temperature, said storage temperature is less than about 15° C. and greater than a freezing point of said blood, blood components, or combinations thereof.

3. The method as defined in claim 2, further including the steps of:

g. releasing said pressure in said chamber;

h. removing said chamber from said casing cavity;

i. removing said bag from cavity of said chamber; and, j. warming said bag above said storage temperature.

4. The method as defined in claim 3, further including the step of shaking, stirring, or combination thereof of said blood, blood components, or combinations thereof in said bag prior to a transfusion to a patient.

5. The method as defined in claim 4, further including the step of orienting said bag in a generally horizontal position at said storage temperature.

6. The method as defined in claim 5, wherein said cavity of said chamber is a hermetically-sealable cavity.

7. The method as defined in claim 6, wherein said gas system has a xenon content that is greater than a xenon content naturally occurring in the atmosphere at sea level.

8. The method as defined in claim 7, wherein said at least one gas that at least partially saturates said blood, blood components, or combinations is xenon.

9. The method as defined in claim 8, wherein said gas mixture includes about 50% to 99.9% by volume xenon and about 0% to 50% by volume oxygen.

10. The method as defined in claim 9, wherein said gas mixture is fed to said chamber under pressure that is at least 1 bar above atmospheric pressure at sea level.

11. The method as defined in claim 10, wherein said gas mixture is fed to said chamber while said blood, blood components, or combinations thereof are at a temperature of about 18° C. to 35° C.

12. The method as defined in claim 11, wherein said gas mixture is fed to said chamber until said blood, blood components, or combinations are at least 50% saturated with xenon gas.

13. The method as defined in claim 12, wherein said step of maintaining said bag of blood, blood components, or combinations in said chamber in said presence of said gas mixture is for 0.001-10 hours.

14. The method as defined in claim 13, wherein said step of cooling down said bag cools said blood, blood components, or combinations to a temperature of 0.01° C. to 15° C.

15. The method as defined in claim 13, wherein said chamber includes an inlet channel that fluidly connects said cavity to a casing channel in said high-strength casing to enable a gas source that includes said gas system to be connected to said high-strength casing such that said gas system can flow through said high-strength casing and into said cavity of said chamber.

16. The method as defined in claim 15, wherein said inlet channel is hermetically-sealed to said casing channel when said chamber is positioned in said chamber cavity and said first and second parts of said high-strength casing are connected together.

17. The method as defined in claim 16, wherein said material used to form said high strength casing is at least about 2 times stronger, at least 2 times more rigid, or combinations thereof than a material used to form said chamber.

18. The method as defined in claim 17, wherein said chamber fills at least about 70% of a volume of said chamber cavity when said chamber is positioned in said chamber cavity.

19. The method as defined in claim 18, wherein said high-strength casing includes a plurality of strengthening ribs that form a honeycomb structure on an outside of said high strength casing.

20. The method as defined in claim 19, wherein said high-strength casing includes connecting flanges to join together a plurality of parts of said high-strength casing, at least one of said connecting flanges includes a fastening element that connects to another connecting flange.

21. The method as defined in claim 20, wherein said high-strength casing includes at least one end-to-end inlet channel, at least one end of said end-to-end inlet channel is designed to connect to at least one end of an end-to-end inlet channel that is located on a second high-strength casing to enable a plurality of high-strength casings to be fluidly connected together and to be supplied by a single gas source that includes said gas system.

22. The method as defined in claim 21, wherein said high-strength casing includes at least one drainage or release valve designed to release gas from the chamber.

23. The method as defined in claim 22, wherein said high-strength casing includes at least one projection on an exterior surface designed to engage an outer surface of another high-strength casing so as to orient, connect, or combinations thereof the two high-strength casings when positioned together.

24. A method for platelet concentrate storage comprising:

a. placing blood, blood components, or combinations thereof in a hermetically-sealed bag, said bag is formed of a material permeable to a gas system that includes at least 5 vol. % xenon gas;

b. placing the bag in a cavity of a chamber, said chamber including first and second chamber parts that form said cavity when connected together;

c. connecting together said first and second chamber parts to hermetically seal said bag in said cavity of said chamber;

d. placing said chamber that includes said bag into a chamber cavity of a high-strength casing, said high-strength casing including first and second casing parts that at least partially form said casing cavity when connected together;

e. feeding said gas system into said cavity of said chamber to at least partially saturate said blood, blood components, or combinations thereof in said bag with xenon, said gas system fed to said hermetically-sealed chamber under a pressure that is greater than atmospheric pressure at sea level; and, f. maintaining said bag of said blood, blood components, or combinations in said cavity of said chamber in said presence of said gas system for at least 0.001 hours.

25. The method as defined in claim 24, wherein said gas system includes oxygen.

26. The method as defined in claim 25, wherein said step of feeding said gas system into said cavity of said chamber includes maintaining said blood, blood components, or combinations in said bag at a temperature of at least about 15° C. while said gas system is fed into said cavity of said chamber.

27. The method as defined in claim 26, further including the step of:
f. after said blood, blood components, or combinations thereof in said bag have reached a desired saturation of said xenon gas, cooling said bag that contains said blood, blood components, or combinations thereof in a cooling system to a storage temperature, said storage temperature is less than about 15° C. and greater than a freezing point of said blood, blood components, or combinations thereof;
g. releasing said pressure in said hermetically-sealed chamber to allow gas in said bag to reach at least partial equilibrium with said ambient atmosphere;
h. removing said chamber from said chamber cavity;
i. removing said bag from cavity of said chamber; and,
j. warming said bag above said storage temperature.

28. The method as defined in claim 27, further including the step of orienting said bag in a horizontal position at said storage temperature.

29. The method as defined in claim 28, further including the step of shaking, stirring, or combination thereof of said blood, blood components, or combinations thereof in said bag prior to a transfusion to a patient.

30. The method as defined in claim 29, wherein said chamber includes an inlet channel that fluidly connects said cavity to a casing channel in said high-strength casing to enable a gas source that includes said gas system to be connected to said high-strength casing such that said gas system can flow through said high-strength casing and into said cavity of said chamber.

31. The method as defined in claim 30, wherein said inlet channel is hermetically sealed to said casing channel when said chamber is positioned in said casing cavity and said first and second parts of said high-strength casing are connected together.

32. The method as defined in claim 31, wherein a material used to form said high-strength casing is at least about two times stronger and at least two times more rigid than a material used to form said chamber.

33. The method as defined in claim 32, wherein said hermetically-sealed chamber fills at least about 70% of a volume of said casing cavity when said hermetically-sealed chamber is positioned in said casing cavity.

34. The method as defined in claim 33, wherein said high-strength casing includes a plurality of strengthening ribs that form a honeycomb structure on an outside of said high strength casing.

35. The method as defined in claim 34, wherein said high-strength casing includes connecting flanges to join together a plurality of parts of said high-strength casing, at least one of said connecting flanges includes a fastening element that connects to another connecting flange.

36. The method as defined in claim 35, wherein said high-strength casing includes at least one end-to-end inlet channel, at least one end of said end-to-end inlet channel is designed to connect to at least one end of an end-to-end inlet channel that is located on a second high-strength casing to enable a plurality of high-strength casings to be fluidly connected together and to be supplied by a single gas source that includes said gas system.

37. The method as defined in claim 36, wherein said high-strength casing includes at least one drainage or release valve designed to release gas from the chamber.

38. The method as defined in claim 37, wherein said high-strength casing includes at least one projection on an exterior surface designed to engage an outer surface of another high-strength casing so as to orient, connect, or combinations thereof the two high-strength casings when positioned together.

39. The method as defined in claim 24, wherein said step of feeding said gas system into said cavity of said chamber includes maintaining said blood, blood components, or combinations in said bag at a temperature of at least about 15° C. while said gas system is fed into said cavity of said chamber.

40. The method as defined in claim 24, further including the step of:
f. after said blood, blood components, or combinations thereof in said bag have reached a desired saturation of said xenon gas, cooling said bag that contains said blood, blood components, or combinations thereof in a cooling system to a storage temperature, said storage temperature is less than about 15° C. and greater than a freezing point of said blood, blood components, or combinations thereof;
g. releasing said pressure in said hermetically-sealed chamber to allow gas in said bag to reach at least partial equilibrium with said ambient atmosphere;
h. removing said chamber from said chamber cavity;
i. removing said bag from cavity of said chamber; and,
j. warming said bag above said storage temperature.

41. The method as defined in claim 24, further including the step of orienting said bag in a horizontal position at said storage temperature.

42. The method as defined in claim 24, further including the step of shaking, stirring, or combination thereof of said blood, blood components, or combinations thereof in said bag prior to a transfusion to a patient.

43. The method as defined in claim 24, wherein said chamber includes an inlet channel that fluidly connects said cavity to a casing channel in said high-strength casing to enable a gas source that includes said gas system to be connected to said high-strength casing such that said gas system can flow through said high-strength casing and into said cavity of said chamber.

44. The method as defined in claim 43, wherein said inlet channel is hermetically sealed to said casing channel when said chamber is positioned in said casing cavity and said first and second parts of said high-strength casing are connected together.

45. The method as defined in claim 24, wherein a material used to form said high-strength casing is at least about two times stronger and at least two times more rigid than a material used to form said chamber.

46. The method as defined in claim 24, wherein said hermetically-sealed chamber fills at least about 70% of a volume of said casing cavity when said hermetically-sealed chamber is positioned in said casing cavity.

47. The method as defined in claim 24, wherein said high-strength casing includes a plurality of strengthening ribs that form a honeycomb structure on an outside of said high strength casing.

48. The method as defined in claim 24, wherein said high-strength casing includes connecting flanges to join together a plurality of parts of said high-strength casing, at least one of said connecting flanges includes a fastening element that connects to another connecting flange.

49. The method as defined in claim 24, wherein said high-strength casing includes at least one end-to-end inlet channel, at least one end of said end-to-end inlet channel is designed to connect to at least one end of an end-to-end inlet channel that is located on a second high-strength casing to enable a plurality of high-strength casings to be fluidly connected together and to be supplied by a single gas source that includes said gas system.

50. The method as defined in claim 24, wherein said high-strength casing includes at least one drainage or release valve designed to release gas from the chamber.

51. The method as defined in claim 24, wherein said high-strength casing includes at least one projection on an exterior surface designed to engage an outer surface of another high-strength casing so as to orient, connect, or combinations thereof the two high-strength casings when positioned together.

* * * * *